(12) United States Patent
Virta et al.

(10) Patent No.: US 6,466,641 B1
(45) Date of Patent: Oct. 15, 2002

(54) CRANIAL RADIOGRAPHY APPARATUS

(75) Inventors: Arto Virta, Helsinki (FI); Liina Nyholm, Helsinki (FI); Timo Müller, Espoo (FI)

(73) Assignee: Planmeca Oy, Helsinki (FI)

( * ) Notice: Subject to any disclaimer, the term of this patent is extended or adjusted under 35 U.S.C. 154(b) by 0 days.

(21) Appl. No.: 09/509,714

(22) PCT Filed: Oct. 2, 1998

(86) PCT No.: PCT/FI98/00778

§ 371 (c)(1),
(2), (4) Date: Jun. 26, 2000

(87) PCT Pub. No.: WO99/17659

PCT Pub. Date: Apr. 15, 1999

(30) Foreign Application Priority Data

Oct. 2, 1997 (FI) .................................................. 973872

(51) Int. Cl.[7] .................................................. A61B 6/14
(52) U.S. Cl. ............................................................ 378/38
(58) Field of Search ..................................... 378/38–40

(56) References Cited

U.S. PATENT DOCUMENTS 5,355,398 A * 10/1994 Nakano et al. ............... 378/40
5,511,106 A * 4/1996 Doebert et al. ............... 378/40

* cited by examiner

Primary Examiner—Craig E. Church
(74) Attorney, Agent, or Firm—Steinberg & Raskin

(57) ABSTRACT

The present invention relates to a cranial radiography apparatus, particularly intended for dental panoramic radiography, said apparatus comprising a first body part to which is connected a second body part (13) having thereto connected a third body part (14) to which is connected a fourth body part (15). To the opposite ends of said fourth body part (15) are connected an x-ray source and an x-ray detector. The body parts are connected to each other by means of pivot shafts aligned essentially parallel to each other. The pivot shafts are rotated by means of active actuators and their rotational movement is programmably controlled by means of a computer, thus permitting the x-ray source and the x-ray detector to be moved over any predetermined orbit. The apparatus further includes means for radiography using a cephalostat. The apparatus can be adapted for robotic change of the x-ray detector by virtue of said movements of the body parts of the apparatus and a storage post designed to store the x-ray detectors used in different radiography modes.

21 Claims, 23 Drawing Sheets

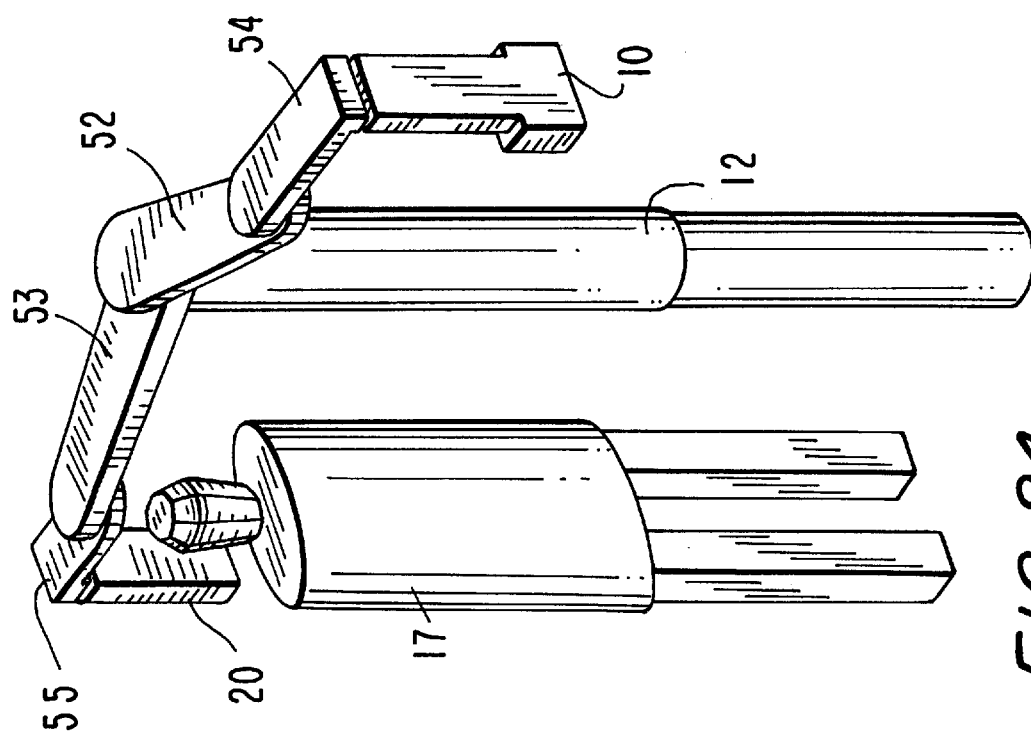
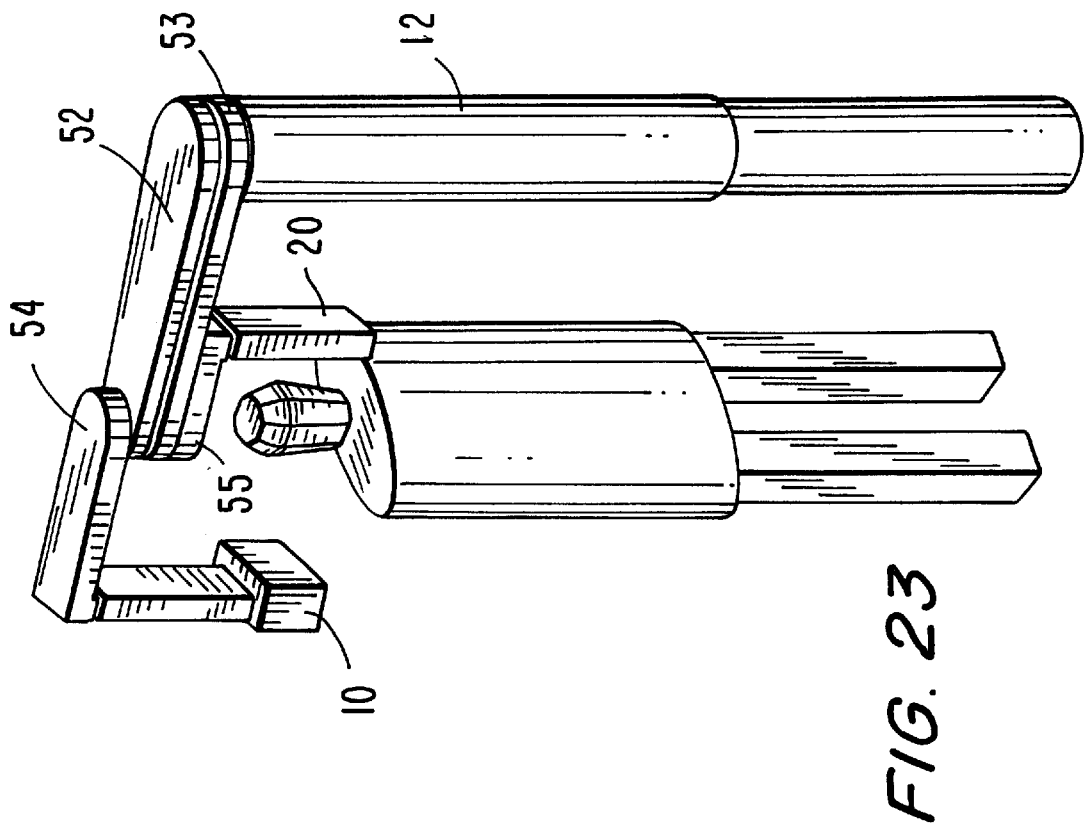
FIG. 24
FIG. 23

CRANIAL RADIOGRAPHY APPARATUS

FIELD OF THE INVENTION

The present invention relates to a cranial radiography apparatus, particularly intended for dental radiography, said apparatus comprising a first body part to which is connected a second body part, the other end of which being connected to a third body part, whose other end carries a fourth body part having an x-ray source mounted at its one end and an x-ray detector at its other end and in which apparatus said second body part and said third body part are connected to each other via a first pivot shaft and, further, said third body part and said fourth body part are connected to each other via a second pivot shaft, both of said pivot shafts being essentially parallel to each other.

BACKGROUND OF THE INVENTION

The most important tasks of radiography in regard to cranial imaging of the human skull include panoramic tomography of the dental arch, radiography of the dental arch in a transverse plane, radiography of the temporomandibular joints and cephalometric radiography of the whole skull. These imaging tasks can be accomplished using a variety of different radiographic techniques: narrow-beam tomography, linear tomography, full-field fluoroscopy, slit fluoroscopy, tomosynthesis radiography and computerized tomography, for instance. In some radiographic apparatus configurations, these different imaging modes can be carried out in the one and the same apparatus by making certain arrangements in the apparatus prior to commencing the radiographic operation and by selecting a suitable control program for the imaging operation. One of the most important and also most demanding radiographic imaging modes in the use of radiographic equipment is panoramic tomography whose basics are next described in greater detail.

Conventional panoramic radiography apparatuses are characterized in that the x-ray source is arranged to orbit about the patient's skull, whereby the dental arch can be imaged by means of an x-ray detector orbiting on the opposite side of the scull. The image can be formed either directly on a film or stored by means of various types of solid-state detectors such as a CCD array sensor in digital format and then displayed on a screen.

In order to obtain a sharp image from a desired object, e.g., the dental arch, the sweep velocity of the x-ray detector must be equal to the sweep velocity of the x-ray beam over the object multiplied by the magnification. Then, the undesirable structures of the object being imaged are blurred invisible. The magnification is determined by the distance between the x-ray tube focus and the film plane to the distance between the x-ray tube focus and the object.

The thickness of the sharply imaged tissue layer is linearly proportional to the distance of the center of rotation to the x-ray detector plane and inversely proportional to the magnification and the beam width. Hence, the imaging process is only related to the mutual dispositions of the focus, the object and the x-ray detector plane.

The basic equation of panoramic imaging is expressed as follows:

$$v_1/v_0 = L_1/L_0$$

$v_O = \omega r$, where $L_O$=distance from tube focus F to the point of the object being imaged $L_1$=distance from tube focus F to the x-ray detector plane $\omega$=angular velocity of rotational movement about the center of rotation r=distance of the object point being imaged from the center of rotation $v_1$=velocity of the image point over the film or x-ray detector plane.

The function of the rotating mechanism of a panoramic tomography apparatus is to direct the x-ray beam through the patient's jaw at a desired angle and to keep the x-ray detector at a given distance from the object being imaged. During the rotational movement, the center of rotation is moved in order to fulfill the following criteria:

orthogonality: the x-ray beam shall be incident on the object as orthogonally as possible in order to prevent adjacent teeth from overlapping at any point of the recorded image;

constant magnification: the magnification shall be maintained constant over the entire dental arch, which requirement can be fulfilled by keeping the distance between the layer being imaged and the image plane of the x-ray detector constant over the entire swept sector of the orbital movement;

motion continuity: the center of rotation shall move monotonously without discontinuities that could cause excessive forces of acceleration and thereby problems in the image quality, and minimization of radiation dose imposed on the patient: the projection image shall be recorded so that the patient will not be exposed to an unnecessarily large dose of radiation.

The x-ray source of the panoramic tomography apparatus and the rotating mechanism of its x-ray detector must be capable of forming a projection image that satisfies the above-stated requirements set for the recording of the projection radiograph. Furthermore, the apparatus must have a design that can be manufactured at a reasonable cost to a precision free from slack causing disturbing inaccuracies in the recording of a radiograph, such as excessive play between the different elements of the rotating/translating mechanism. Hence, said mechanism must be able to accomplish the desired orbital movement of the center of rotation in a horizontal plane and, additionally, provide vertical support to the entire apparatus so that the desired orbit can be implemented with a good accuracy.

Such an orbital movement can be achieved by virtue of different conventional rotating mechanisms. In the embodiment disclosed in applicant's patent FI 73091 (corresponding U.S. Pat. No. 4,741,007), the orbital movement is accomplished by means of two pivot shafts placed at a constant distance from each other. This construction forms the orbital geometry of the imaging process with the help of a guide groove and an active actuator.

Another prior-art technique for producing the orbital movement is the method disclosed in patent FI 87135 (filed by Instrumentarium Oy), in which the mutual distance between the pivot shafts is made variable. Hence, the orbital movement can be generated as a combination of the rotational movement and the linear movement, thus offering a freely variable orbital geometry of the imaging process.

However, the combination of a linear movement with a rotational movement has been found problematic to implement due to the demanding accuracy requirements of the orbital movement. This is because more difficult to obtain the same accuracy for the mechanism of the orbital movement when a linear movement is involved than when a rotational movement is employed alone.

In prior-art constructions, the generation of the orbital geometry has been optimized particularly for panoramic tomography. Simultaneously, the implementation of other radiographic imaging modes has generally become clumsy if not even impossible.

OBJECTS AND SUMMARY OF THE INVENTION

It is an object of the present invention to provide a method of accomplishing a rotational movement in a manner capable of providing accurate orbital geometries at more reasonable equipment costs than those of conventional constructions and simultaneously offering a selection of orbital geometries facilitating flexible switching between different cranial imaging modes (including, e.g., panoramic tomography of the dental arch, radiography of the dental arch in transverse projections commonly known as transverse radiography, imaging of the temporomandibular joints and the entire skull) using at all times a radiographic technique most appropriate for the need (e.g., narrow-beam tomography, slice tomography, full-field fluoroscopy, slit fluoroscopy, tomosynthesis radiography or computer tomography).

It is a further nonlimiting object of the invention to provide an apparatus capable of fulfilling the above-described orthogonality requirement with a good accuracy.

It is a still further nonlimiting object of the invention to provide an apparatus capable of keeping constant magnification over the entire imaged area.

It is still another further nonlimiting object of the invention to provide an apparatus capable of offering easy modifiability for cranial radiography.

It is still a further nonlimiting object of the invention to provide an apparatus in which the arms of the orbital mechanism can be readily rotated aside in order to make patient positioning easier.

It is still another further nonlimiting object of the invention to provide an apparatus that can be reorganized into a compact configuration for easier transport and/or storage and lower transport costs.

It is still another further nonlimiting object of the invention to provide an apparatus in which the orbital mechanism can be used for robotic or manual change, fetching and return of x-ray detectors. This function may be advantageously implemented by complementing the basic construction of the apparatus with a storage device for the x-ray detectors, whereby the orbital mechanism can perform under a preset control program such a transfer of the x-ray detectors between said storage device and the radiographic apparatus proper.

To achieve these goals and others to be explained later, the invention is principally characterized in that the fixed distance between said first and said second pivot shaft is used, said third body part is adapted rotatable in respect to said second body part by means of an active actuator, said fourth body part is adapted rotatable in respect to said third body part by means of an active actuator, and the rotational movement of said fourth body part is implemented by means of program-controlled operation of said active actuators, thus forcing the x-ray source and the x-ray detector to move along a predetermined orbit, said orbit defining the desired layer to be imaged sharp from the object being radiographed in tomography.

In the present invention, the rotational movement required in the panoramic exposure is realized by means of rotational movements taking place in the principal plane of the actuated body parts. The number of the body parts can be three or four, whereby the first body part is a stationary member such as a vertical column, most advantageously a telescopic column, or alternatively, a body part or bracket suitable for mounting on a wall or a ceiling. The orbital movement can be implemented most advantageously as a combination rotational movement of two or three body parts. Obviously, a greater number of such arm combinations of rotatable body parts can be used. Then, the movements of the x-ray source and the x-ray detector are realized using separate arm combinations operating independently from each other. This type of orbital mechanism implemented as a combination of rotational movements is commonly known as a SCARA (Selective Compliance Assembly Robot Arm) mechanism. This technique of implementing a movement gives at a reasonable equipment cost an orbital movement of clearly more accurate position control than other methods and equipment known in the art. Furthermore, the SCARA mechanism offers a possibility of robotic change of different types of x-ray detectors.

According to the invention, the first and the second body parts may be connected to each other in a fixed manner, or alternatively, the joint between these body parts can be provided with a pivot shaft driven by an active actuator suitable for program-controlled robotic rotation of said second body part in respect to said first body part, most advantageously about a vertical axis of rotation. The scope of the invention further covers embodiments in which the second body part is mounted by suitable fixtures on the ceiling and/or wall of the radiography room, whereby these arrangements form the first body part defined in the specifications of the invention.

The fourth body part may be formed by a C-arm having the x-ray source mounted at one end of its horizontal part and an x-ray detector at the other end, opposite to said x-ray source. Alternatively, the C-arm may be replaced by two separate members, herein called an L-arm. Such an L-arm comprises a horizontal support part with the x-ray source or the x-ray detector, respectively, mounted thereto. The x-ray source and the x-ray detector, respectively, are mounted so as to permit their free rotation about the vertical axis of the L-arm. The rotational movement is implemented with the help of an active actuator.

According to the invention, the second body part may alternatively comprise two superimposed body parts, both being connected at their one ends to said first body part and having L-arms connected to their distal ends. Such an arm combination may be utilized for the transfer of detachable x-ray detectors between the different parts of the apparatus.

During patient positioning, the arm system of the apparatus can be kept turned aside, whereby an unobstructed access of the patient to the radiography equipment is assured and the positioning of the patient becomes effortless. At the start of the radiographic exposure, the arm system is rotated to above the patient.

The auxiliary arm used in cephalographic exposures may have a shorter length than in conventional equipment, since the arm system of the present panoramic apparatus can be extended efficiently to the limits of the arm movements.

BRIEF DESCRIPTION OF THE DRAWINGS

In the following the invention will be examined in greater detail by making reference to the diagrams of appended drawings illustrating diagrammnatically a few exemplifying embodiments of the invention, whereby the details of the diagrams must not be understood as limiting to the scope of the invention, in which drawings

FIG. 14A shows the situation of FIG. 13 in a side view, while

FIG. 23 shows an alternative embodiment of the apparatus according to the invention in which the orbital movement of the x-ray source and the x-ray detector are accomplished by means of two sets of actuated arms with the arms set ready for a panoramic exposure;

FIG. 24 shows the apparatus of FIG. 23 set ready for a cephalographic exposure.

DETAILED DESCRIPTION OF THE INVENTION

Figure 1:
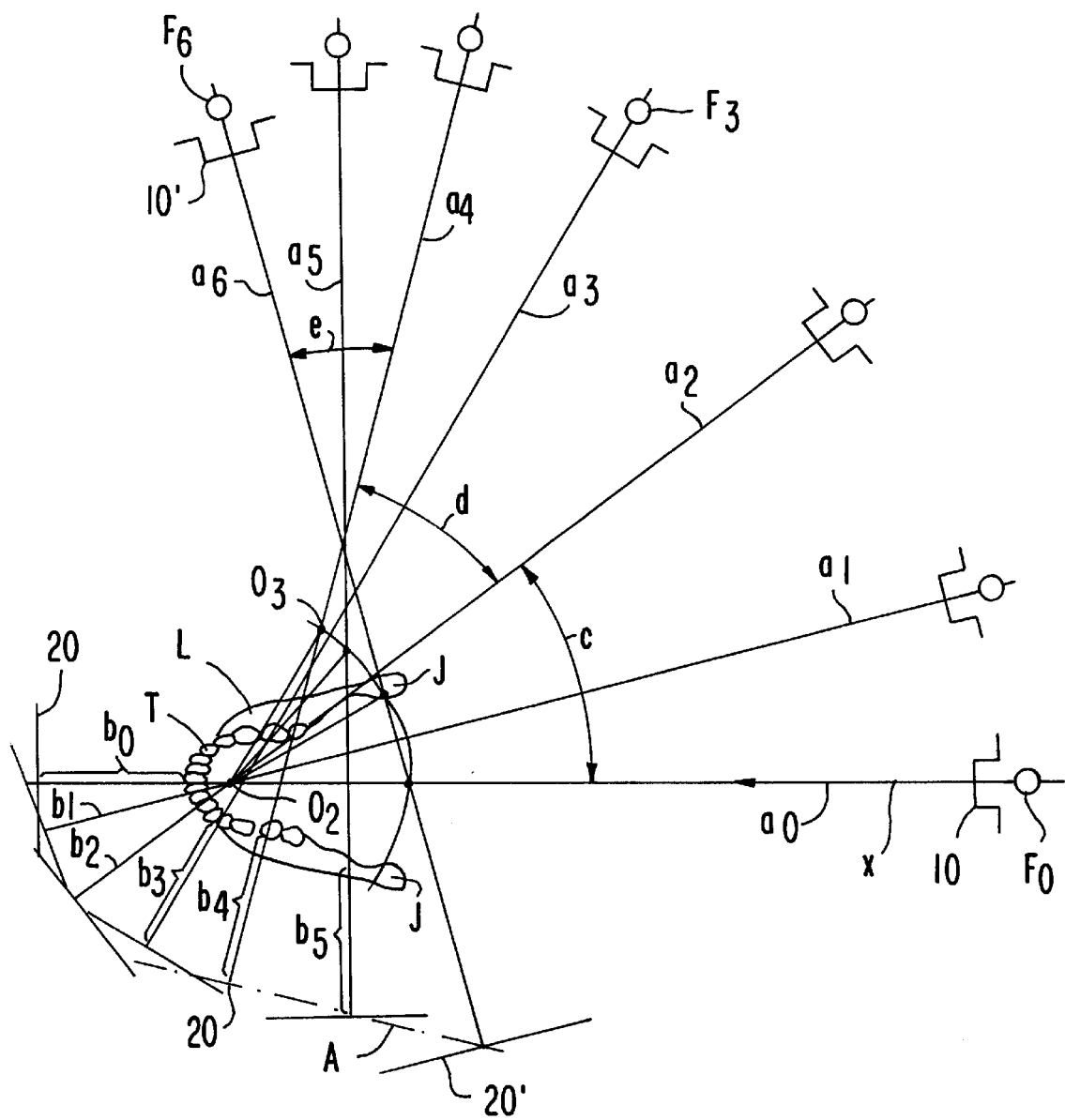
FIG. 1 shows the imaging geometry and the generation of the radiographic projections in a prior art apparatus.

Now referring to FIG. 1, therein is shown the imaging geometry and the generation of the radiographic projections accomplished by means of a prior art apparatus. The x-ray source is denoted by reference numeral 10 and the loci of its tube focus in the different positions by reference symbols $F_0$–$F_6$. The x-ray source 10 emits an x-ray beam X through the teeth T and the jawbone L to an x-ray detector 20 along the line a. The path of the x-ray beam X is shown in FIG. 1 for seven different positions $a_0$–$a_6$. The position of the x-ray source in its one limit position is denoted by reference numeral 10' and, respectively, the x-ray detector by reference numeral 20', whereby the corresponding position of the x-ray tube focus is denoted by reference symbol $F_6$. The temporomandibular joints of the jawbone are denoted by reference symbol J.

In the incisor region of the dental arch, covered by the angle formed between beams $a_0$–$a_2$ (sector c) in the diagram, the rotation of the body part connecting the x-ray source 10 and the x-ray detector 20 occurs in a horizontal plane about a vertical axis of rotation $O_2$. During the orbital movement from beam line $a_2$ to $a_4$ (sector d), the center of rotation $O_2$ moves dynamically along a curved trajectory (not shown) to position $O_3$ of the vertical axis of rotation as shown in the diagram, and therefrom farther away from the center axis $a_0$ (C—C). Using the orbital geometry illustrated in FIG. 1, the orthogonality of the panoramic exposure is realized with a good accuracy both for the incisor region of the dental arch and at the side regions thereof, even up to the temporomandibular joints J at the distal end of the jawbone L. Also the magnification can be maintained constant over the entire imaged area by virtue of the fact that the distance $b_0$–$b_5$ of the x-ray detector from the layer being imaged remains constant with a sufficiently good accuracy over the entire orbit of the exposure.

In the following, a mechanism according to the invention is explained capable of realizing the above-described orbital geometry.

Figure 2:
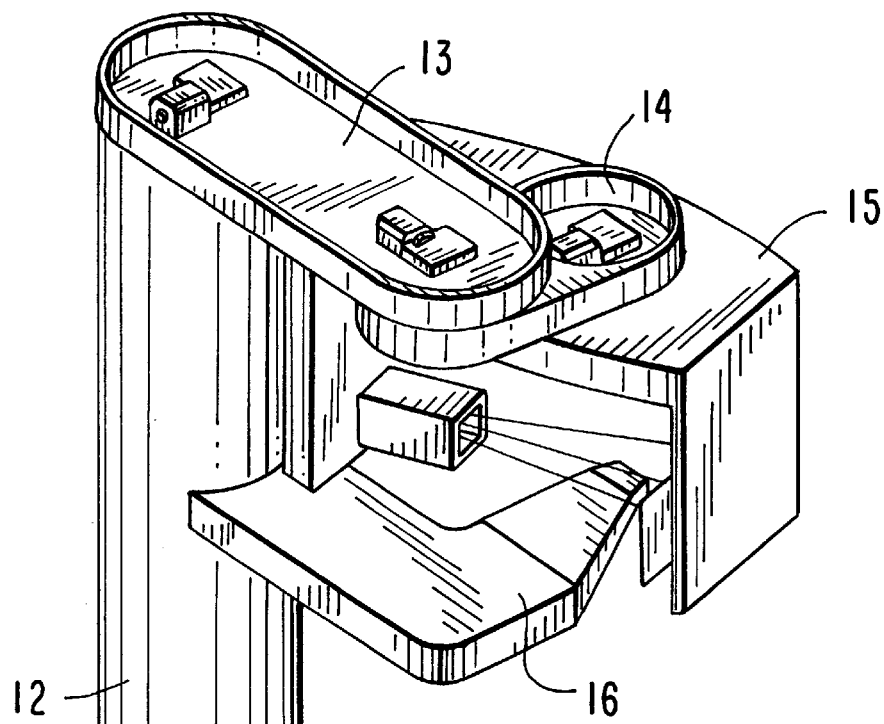
FIG. 2 shows an overall view of a panoramic radiography apparatus according to the invention.

In FIG. 2 are shown the basic components of an apparatus according to the invention; a pedestal 11, a first body part 12, a second body part 13, a third body part 14, a fourth body part 15 and a patient positioning support 16. The first body part 12 may be fastened to the pedestal 11, or alternatively, to a wall or ceiling. The first body part 12 most advantageously comprises a telescopic vertical arm with an adjustable height. Alternatively, the first body part 12 may comprise a stationary upright bracket or similar body part suited for mounting on a wall or ceiling.

Figure 3:
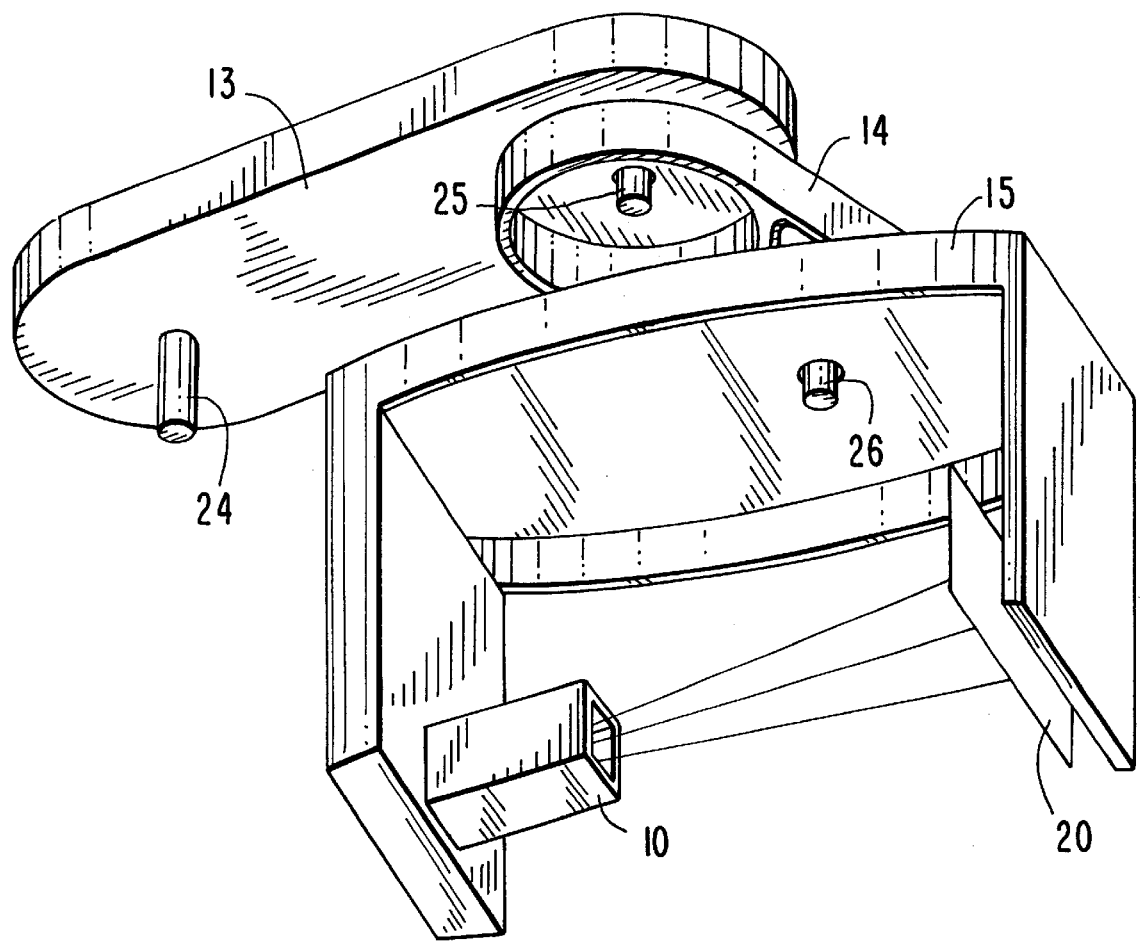
FIG. 3 shows the moving body parts of the apparatus viewed obliquely from below, whereby the pivot shafts connecting the body parts of the apparatus are visible.

In FIG. 3 is illustrated in greater detail the second body part 13, the third body part 14 and the fourth body part 15, the latter having the x-ray source 10 connected to its one end and the x-ray recording device 20 to its other end. The x-ray recording device 20 may be a radiographic film, a CCD sensor or any other type of x-ray detector. The second body part 13 is connected by a vertical pivot shaft 24 to the first body part 12, the third body part 14 is connected by a vertical pivot shaft 25 to the second body part 13, and the fourth body part 15 is connected by a vertical pivot shaft 26 to third body part 14. The invention may alternatively be implemented so that the first body part 12 is replaced by a wall and/or ceiling of the radiography room on which the second body part 13 is mounted directly by suitable fixtures and/or fastening means.

Figure 4:
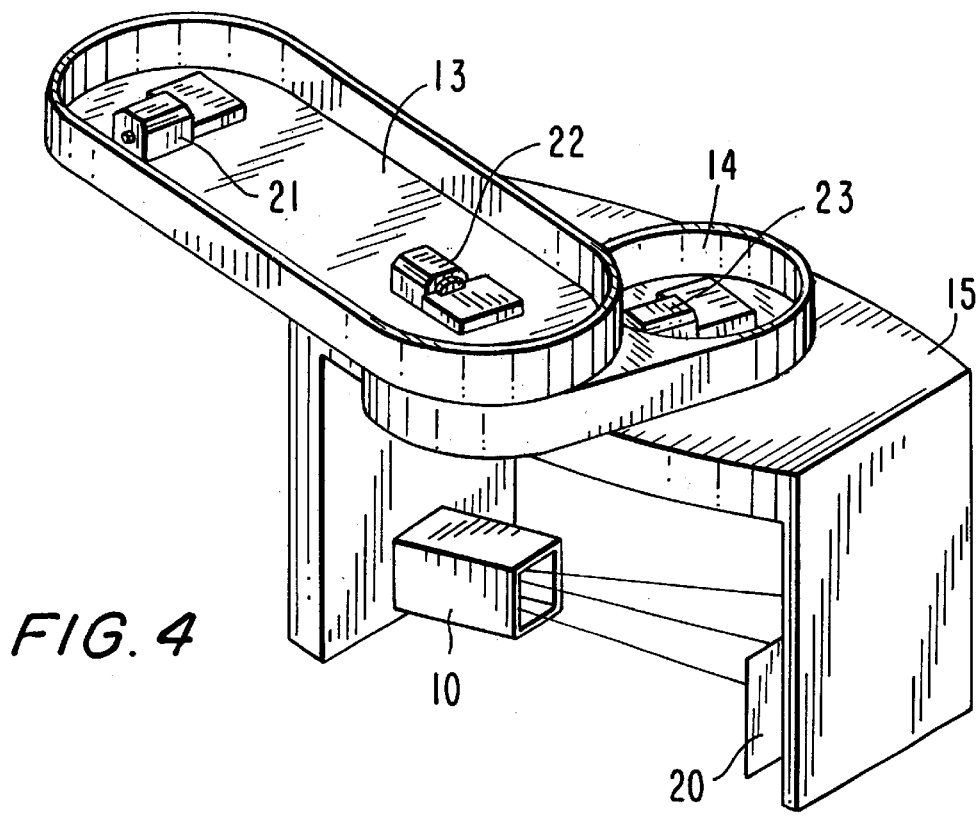
FIG. 4 shows the moving body parts of the apparatus according to the invention with the drive motors of their mutual movements.

In FIG. 4 is shown a situation in which the pivot shafts 24, 25 and 26 are provided with drive motors M (cf. FIG. 5) serving to provide robotic rotation of the body parts about their pivot shafts. To the shaft 24 is connected the drive motor 21 of the second body part 13, to the shaft 25 the drive motor 22 of the third body part 14 and to the shaft 26 the drive motor 23 of the fourth body part 15. Alternatively, the apparatus may be implemented omitting the drive motor of the shaft 24, whereby the pivot shafts 24, 25 and 26 must be provided with essentially zero-play bearings, whose construction is known to be more cost-efficient and simpler than that of conventional linear guides and bearings.

Figure 5:
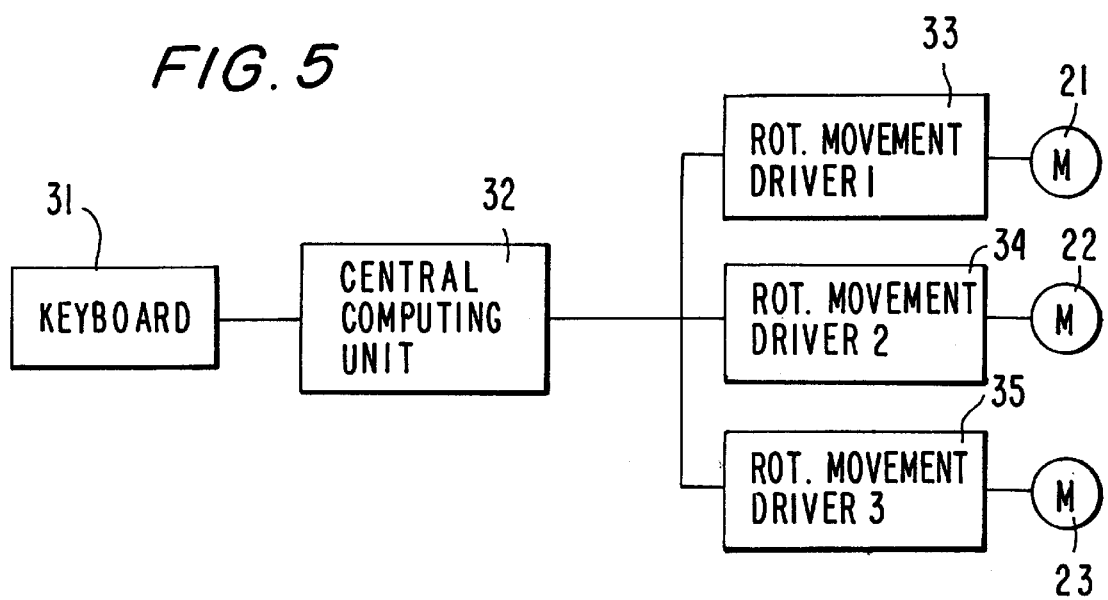
FIG. 5 shows a block diagram of the driver control system of body part actuator motors in the apparatus according to the invention.

In FIG. 5 is shown the block diagram of a driver control system for the drive motors 21, 22 and 23. With the help of a keyboard 31, the required control data is entered into a central computing unit 32 that controls driver 33 of motor 21, driver 34 of motor 22 and driver 35 of motor 23. With the help of this control system, the body parts 13, 14 and 15 can be moved so as to provide any desired orbital geometry for the movement of the fourth body part 15.

Figure 6A:
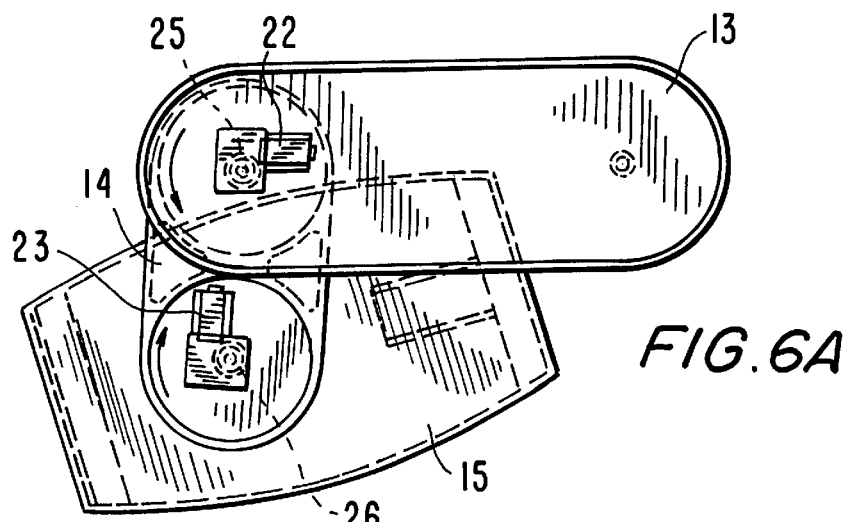
FIGS. 6A, 6B and 6C show the body part positions in the apparatus according to the invention in three phases of panoramic exposure in the case that the second body part is stationary and the third and fourth body parts are actuated to move.
Figure 6B:
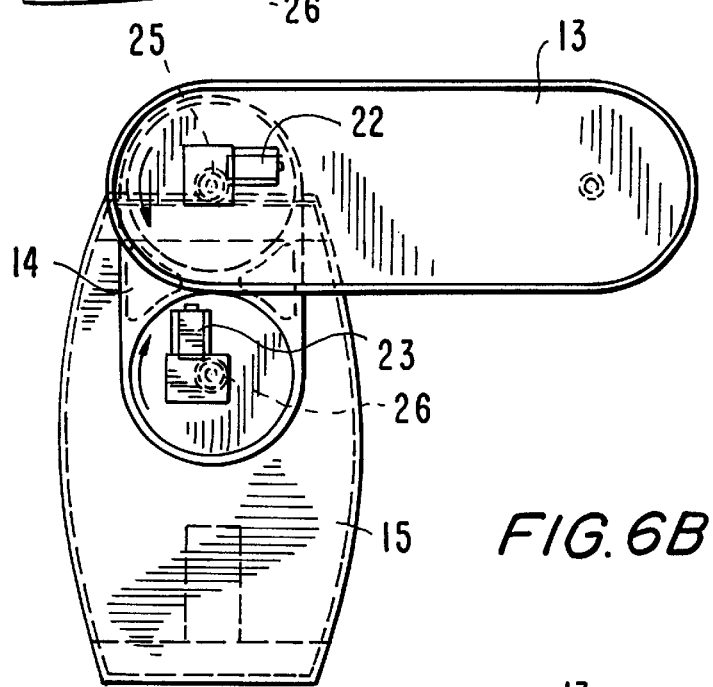
Figure 6C:
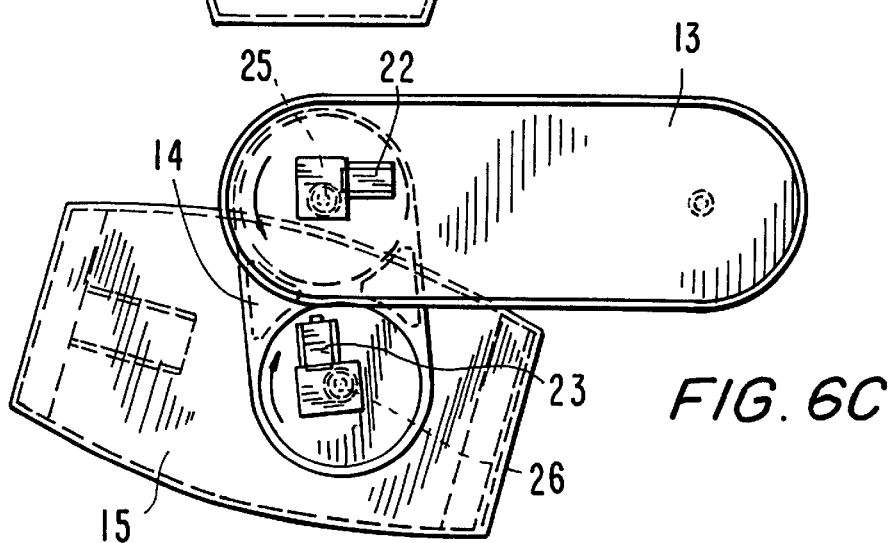

In panoramic tomography, the required orbital geometry can be implemented either so that the second body part 13 remains stationary, or alternatively, so that it participates in the generation of the orbital geometry, too. In FIGS. 6A, 6B and 6C is illustrated an example of the different phases of a panoramic exposure in the case that the second body part 13 is stationary. Herein, FIG. 6A shows the position of the body parts in the beginning of the exposure, FIG. 6B shows their position in the middle of the exposure and in FIG. 6C the position of the body parts is illustrated at the end of the exposure. The directions of rotation for the body parts are denoted by arrows in FIGS. 6A, 6B and 6C. The drive motor 22 of the third body part, which is mounted on the second body part 13, rotates slowly counterclockwise the shaft 25 which connects the second body part 13 to the third body part 14. Simultaneously, the drive motor 22 mounted on the third body part 14 rotates faster clockwise the pivot shaft connecting the third body part 14 to the fourth body part 15.

Figure 7A:
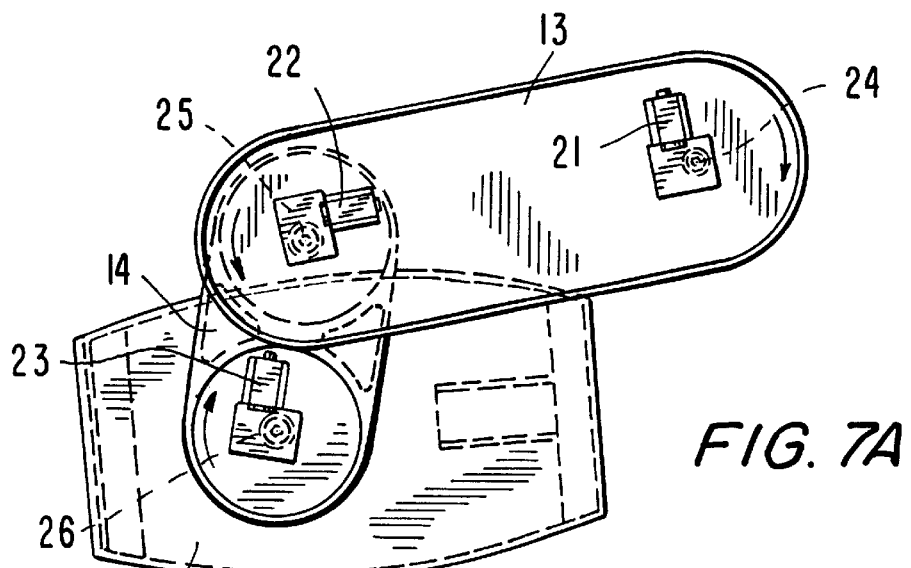
FIGS. 7A, 7B and 7C show the body part positions in the apparatus according to the invention in three phases of radiographic exposure in the case that the second, the third and the fourth body parts are actuated to move so as to participate in the generation of the orbital geometry.
Figure 7B:
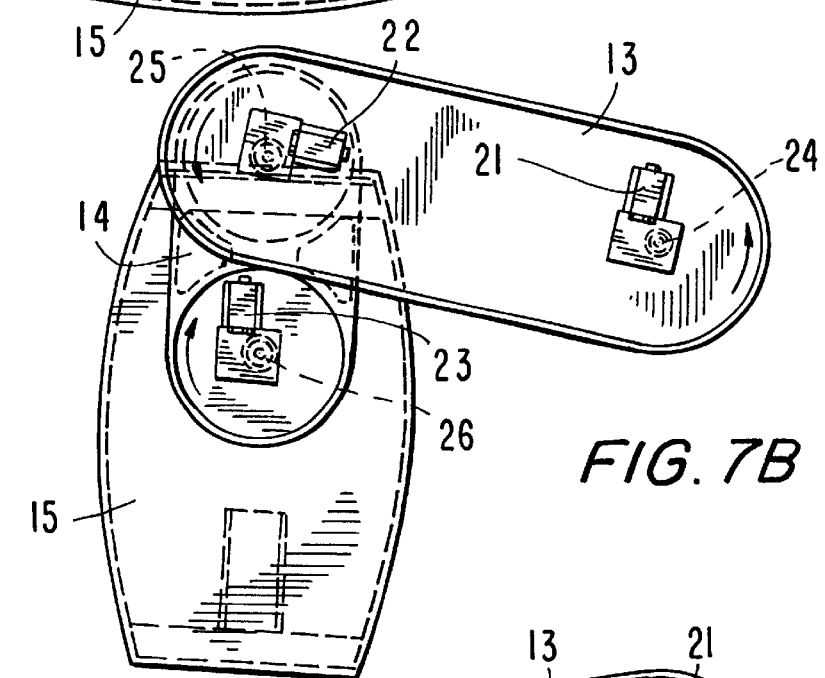
Figure 7C:
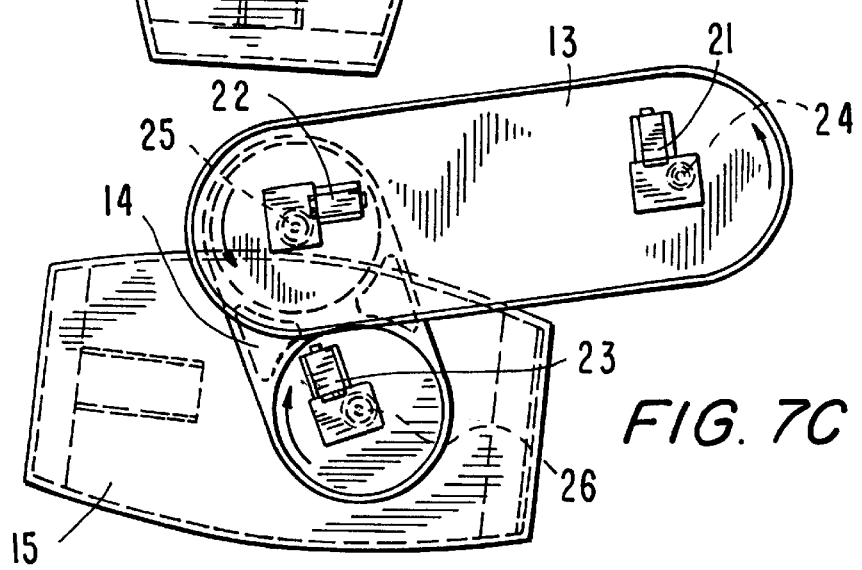

In FIGS. 7A, 7B and 7C is illustrated an example of the different phases of a panoramic exposure in the case that also the second body part 13 participates in the generation of the orbital geometry. Herein, FIG. 7A shows the position of the body parts in the beginning of the exposure, FIG. 7B in the middle of the exposure and in FIG. 7C the position of the body parts is illustrated at the end of the exposure. The directions of rotation for the body parts are denoted by arrows in FIGS. 7A, 7B and 7C in the same fashion as in FIGS. 6A, 6B and 6C. In the beginning of the exposure, the drive motor rotating the second body part is controlled to rotate clockwise (cf. FIG. 7A) the pivot shaft 24 connecting the first body part 12 to the second body part 13, while after passing the mid-point of the exposure, the direction of rotation is changed counterclockwise (cf. FIG. 7B). The drive motor 22 of the third body part, which is mounted on the second body part 13, rotates slowly counterclockwise the shaft 25 which connects the second body part 13 to the third body part 14. Simultaneously, the drive motor 22 mounted on the third body part 14 rotates faster clockwise the pivot shaft connecting the third body part 14 to the fourth body part 15. The drive motors 21, 22 and 23 are most advantageously stepping motors or similar pulse-controlled actuator devices.

Figure 8:
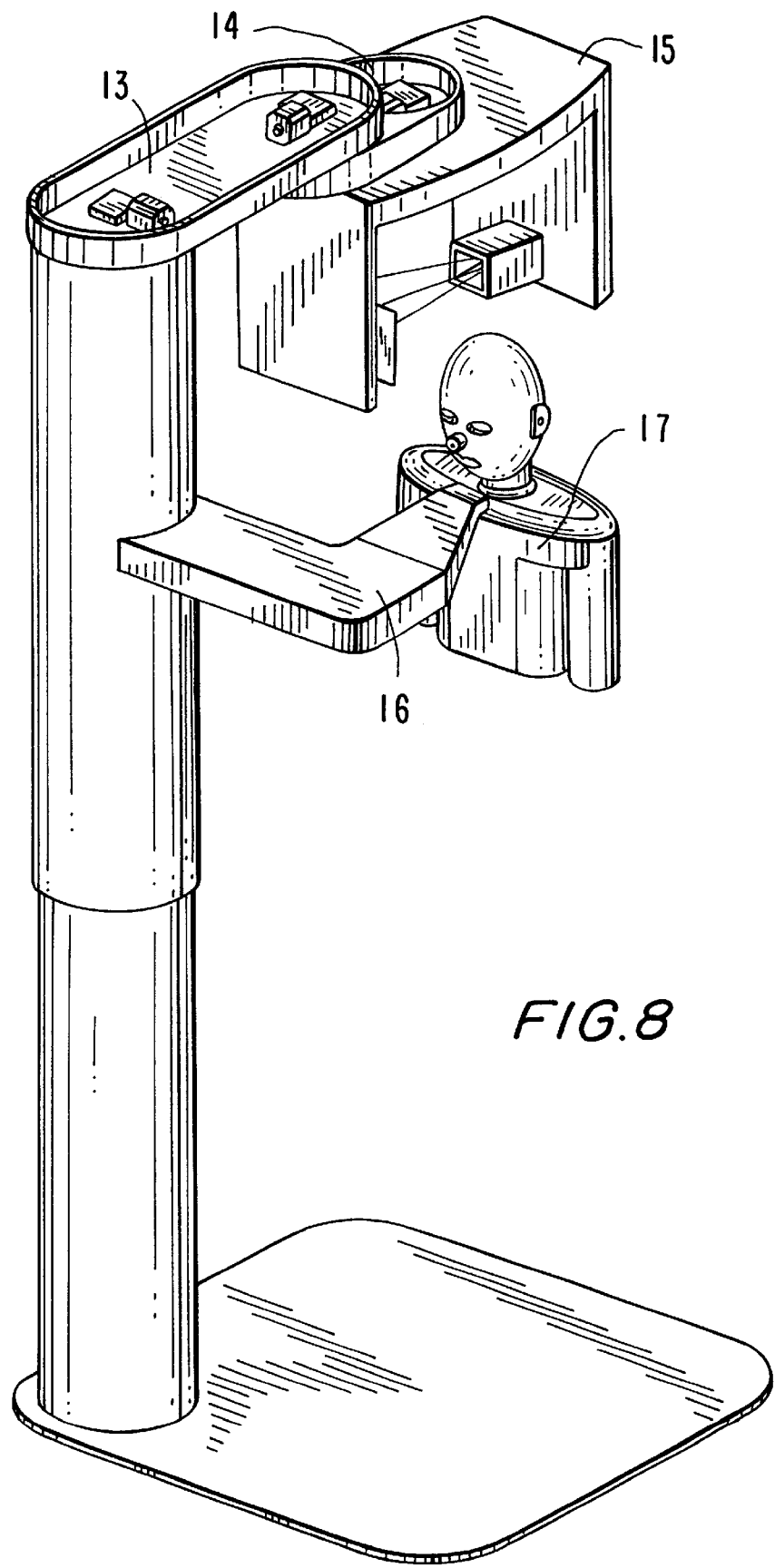
FIG. 8 shows the apparatus according to the invention during patient positioning.
Figure 9:
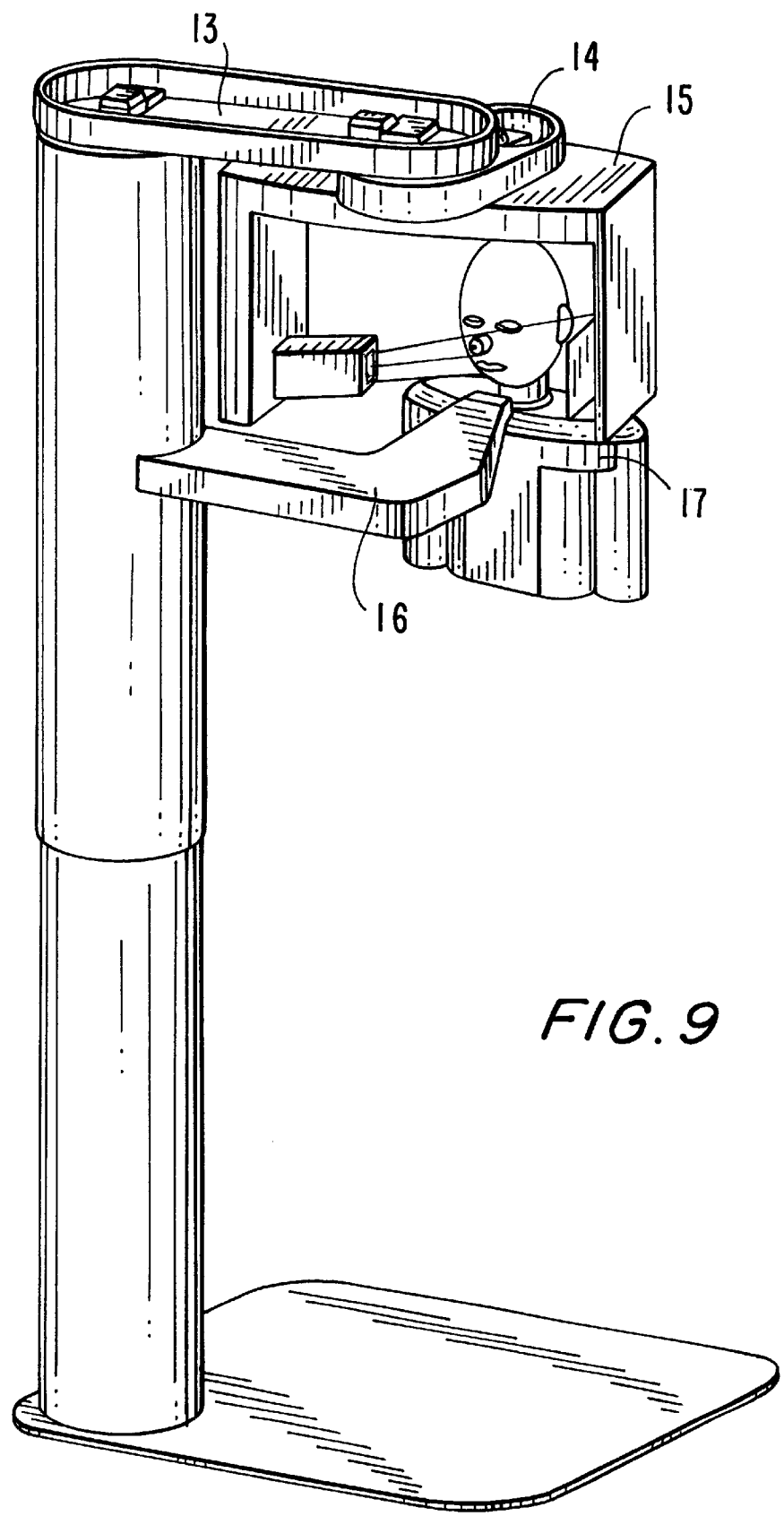
FIG. 9 shows the apparatus according to the invention in the initial phase of a panoramic exposure.

Prior to starting the exposure, all moving body parts are turned aside thus providing an unobstructed access of the patient 17 to the positioning support 16 and allowing unhindered alignment of the patient 17 by the operating personnel into a correct position for the exposure. In FIG. 8 the patient 17 is illustrated properly positioned. After the positioning of the patient 17, the movable body parts of the apparatus are driven either robotically or manually into their initial positions for commencing the exposure as shown in FIG. 9.

Figure 10A:
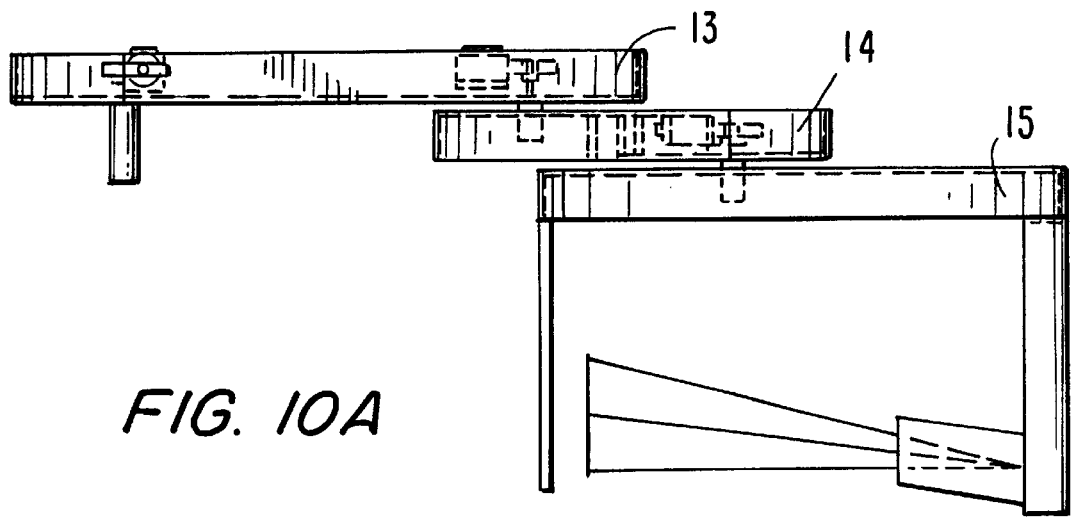
FIG. 10 shows the body parts of the apparatus according to the invention driven to their extreme limit positions.
Figure 10B:
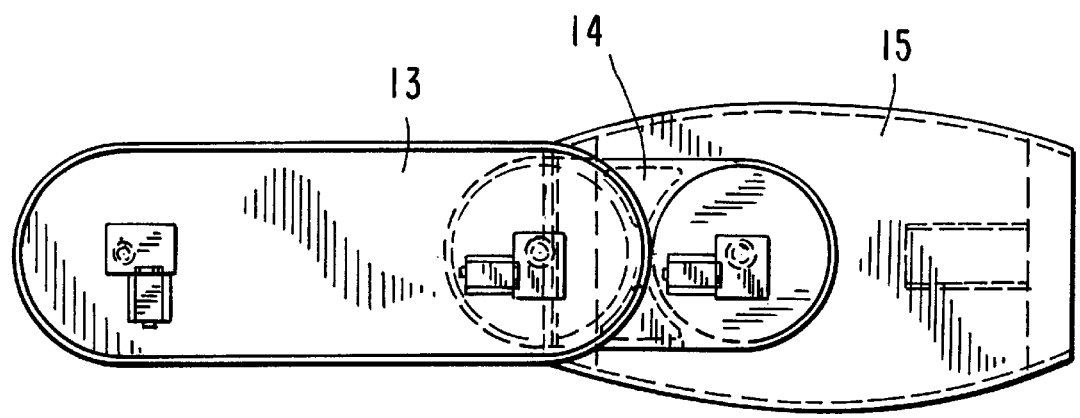

In FIG. 10A is shown in a side view the mutual disposition of the body parts 13, 14 and 15 when they are controlled to their extreme limit positions. In FIG. 10B is shown the same situation viewed from above. As compared to conventional panoramic radiography equipment, the invention makes it possible to bring the x-ray source clearly farther away from the body of the radiographic apparatus, which offers improved capabilities in cephalometric radiography.

Figure 11:
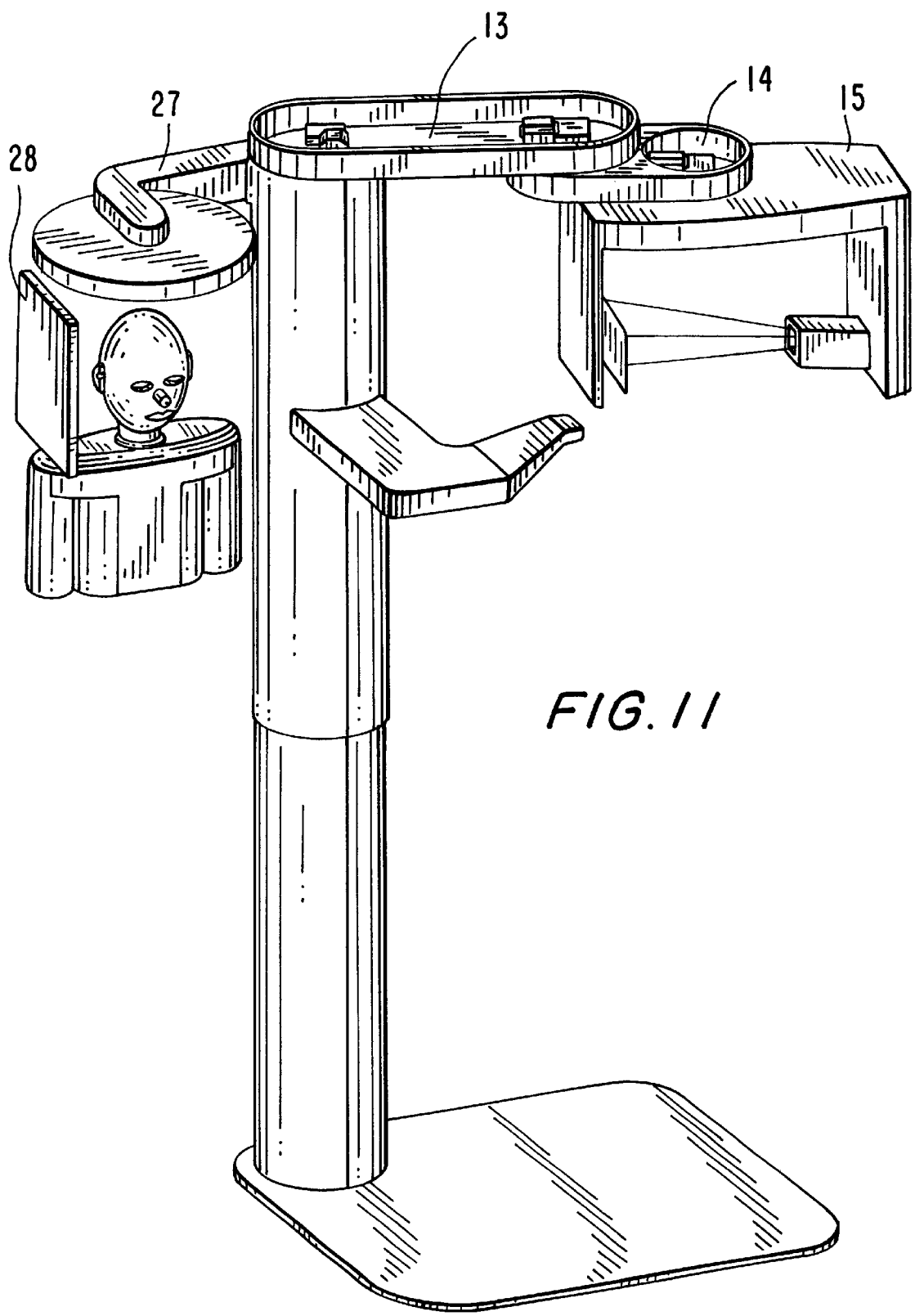
FIG. 11 shows the apparatus according to the invention prepared for a cephalographic exposure.

In FIG. 11 is shown the construction of an apparatus according to the invention modified for cephalometric exposures. Herein, the apparatus is complemented with a cephalostat support arm 27 and an x-ray detector 28 suited for cephalography.

Figure 12:
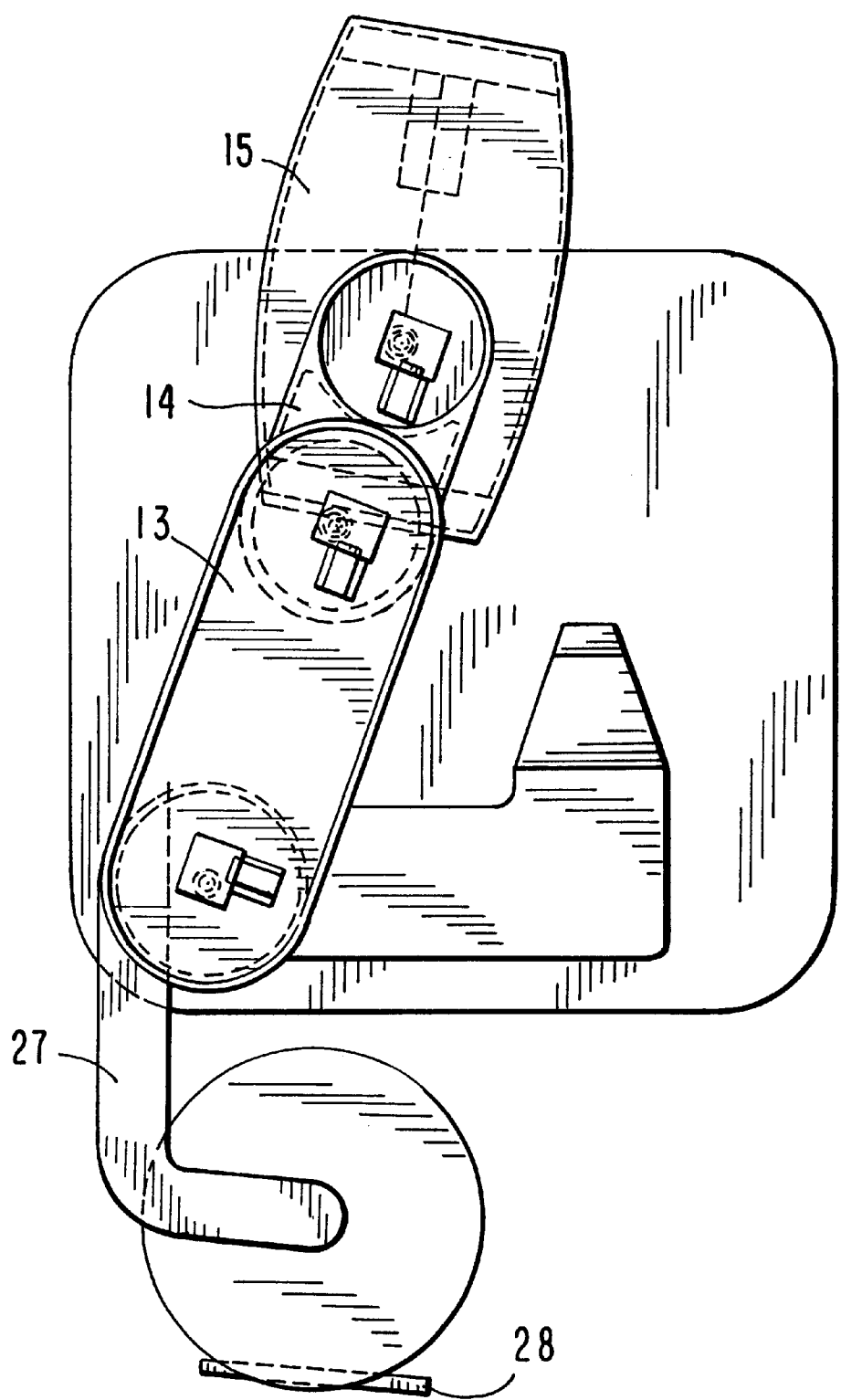
FIG. 12 shows the situation of FIG. 11 viewed from above.

In FIG. 12 are shown in a top view the positions of the body parts 13, 14 and 15, as well as those of the cephalostat auxiliaries 27 and 28.

Figure 13:
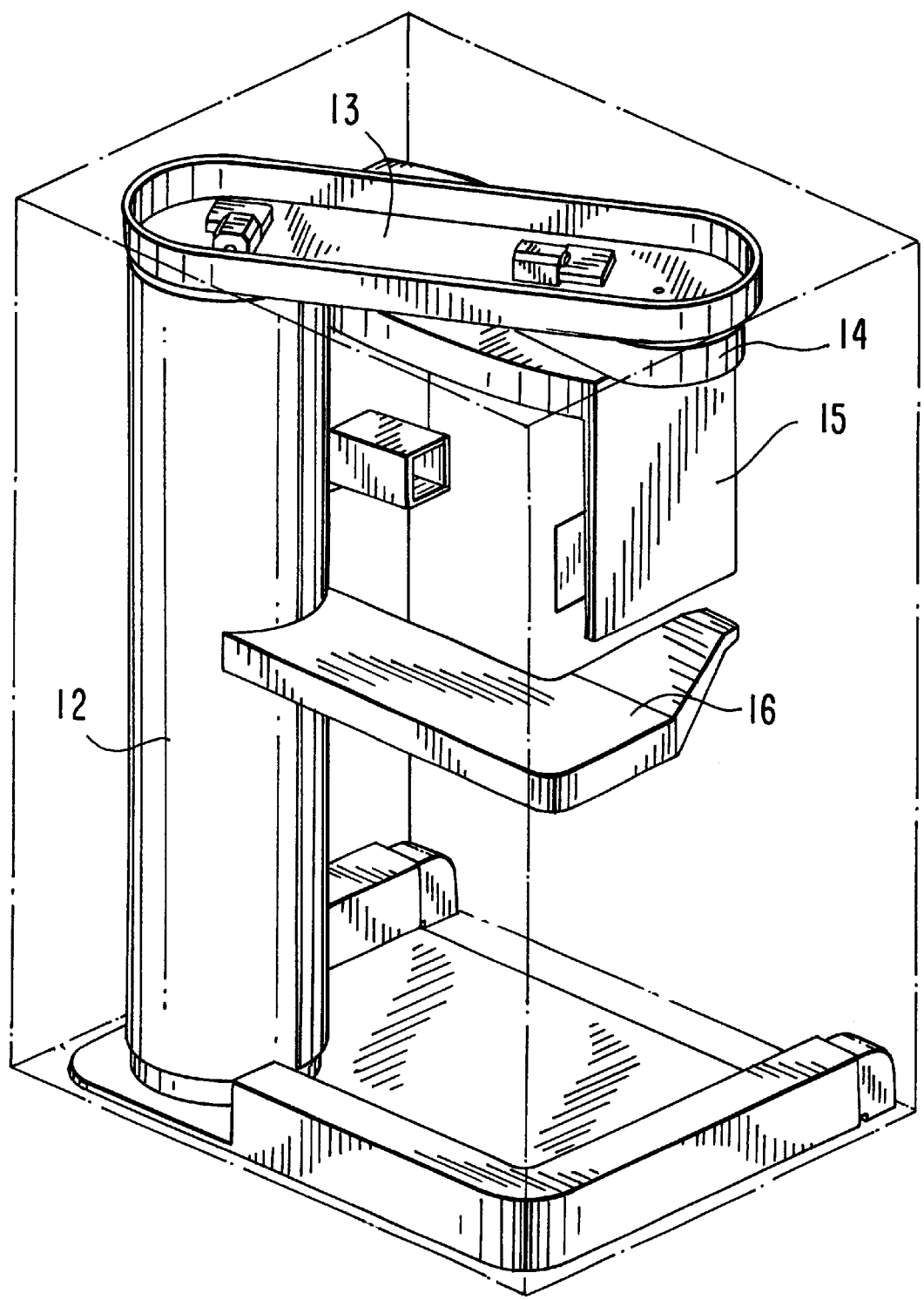
FIG. 13 shows an apparatus according to the invention packed in a transport case in its transport configuration.

In FIG. 13 is shown how an apparatus according to the invention can be placed compactly in a transport case thus minimizing its transport costs. In the configuration illustrated in the diagram, the first body part 12 of the apparatus comprises a telescoping column that is driven into its shortest possible length. The second body part 13, the third body part 14 and the fourth body part 15 are shown articulated above one another into the space above the patient support 16. The compact configuration of the apparatus illustrated in FIG. 13 may also be utilized for storing away the apparatus in a store or a radiographic operating room.

Figure 14A:
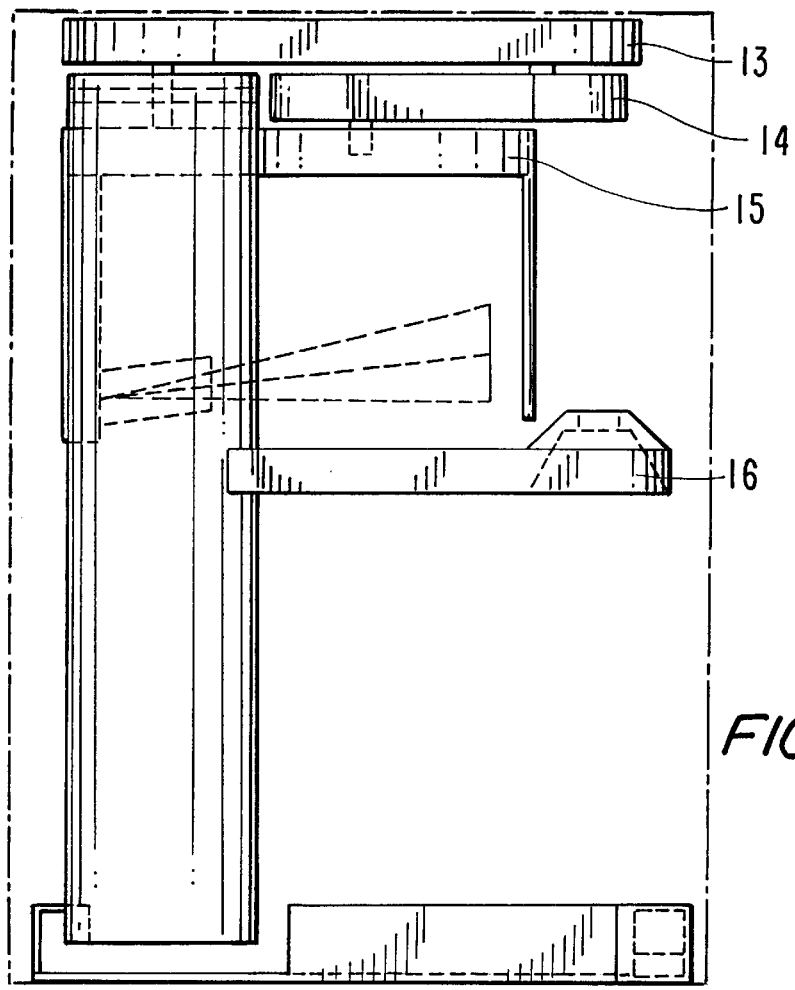
Figure 14B:
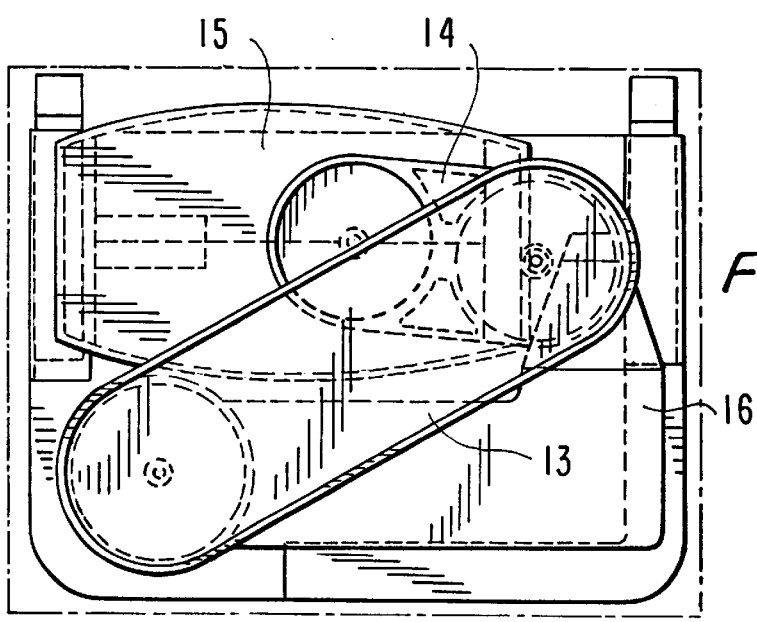
FIG. 14B shows the situation of FIG. 13 viewed from above.

FIG. 14A shows the situation of FIG. 13 from the side and FIG. 14B from above.

Figure 15:
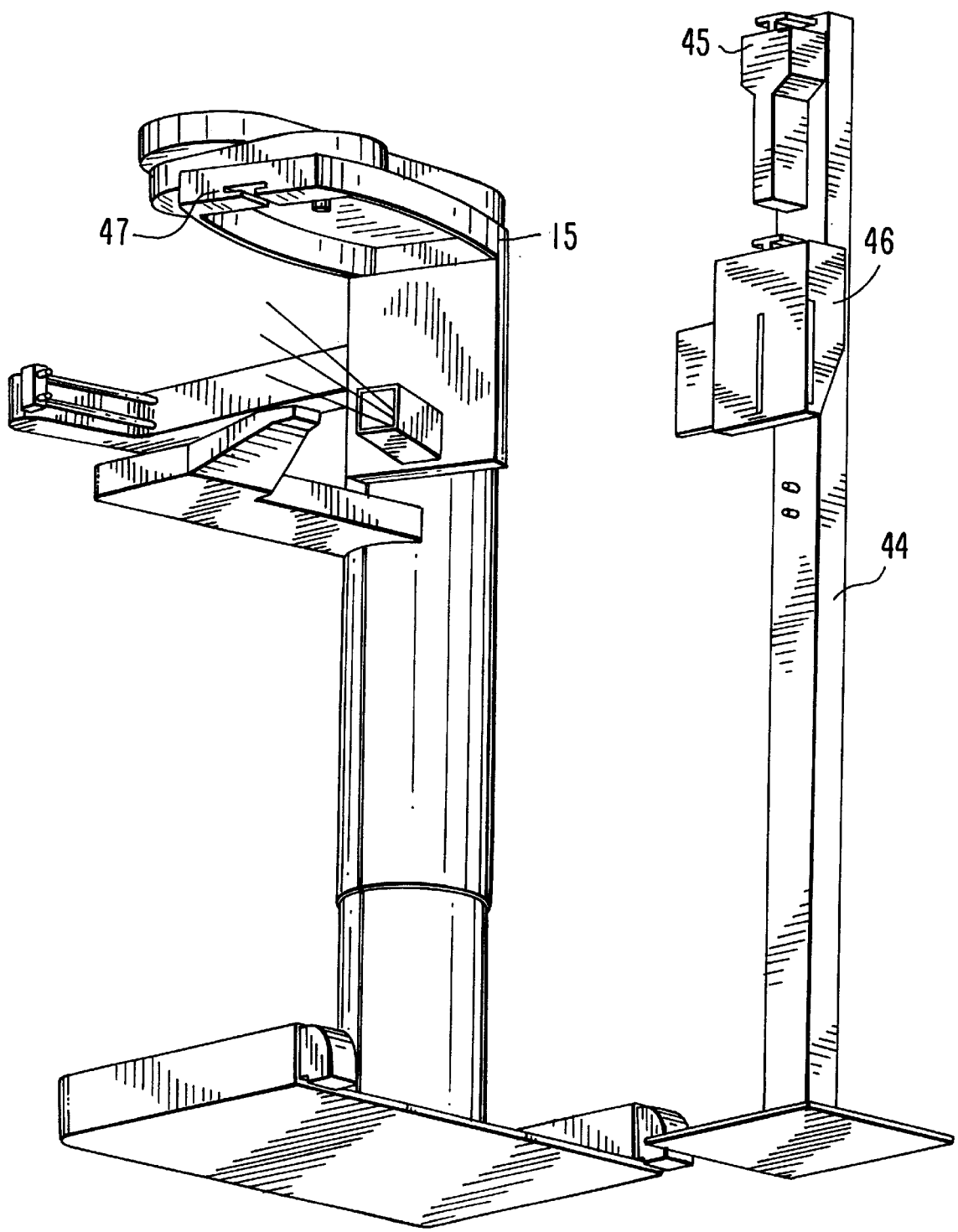
FIG. 15 shows a storage post of different types of x-ray recording devices suitable for mounting beside the apparatus according to the invention.

In FIG. 15 is shown an apparatus according to the invention in which the x-ray detector head of the fourth body part 15 is modified detachable and equipped with a mounting groove 47 for the x-ray detector. Beside the apparatus is installed a storage post 44 with support means for changeable x-ray detectors. The storage post 44 of the radiographic recording means incorporates storage facilities for a number of different types of detectors. Thus a suitable type of detector can be selected for any exposure situation and then the apparatus according to the invention carries out the selection by robotically fetching/mounting the detector. In FIG. 15, the storage post 44 is shown to carry, e.g., uppermost a digital x-ray detector 45 with a radiographic film holder 46 below it.

Figure 16:
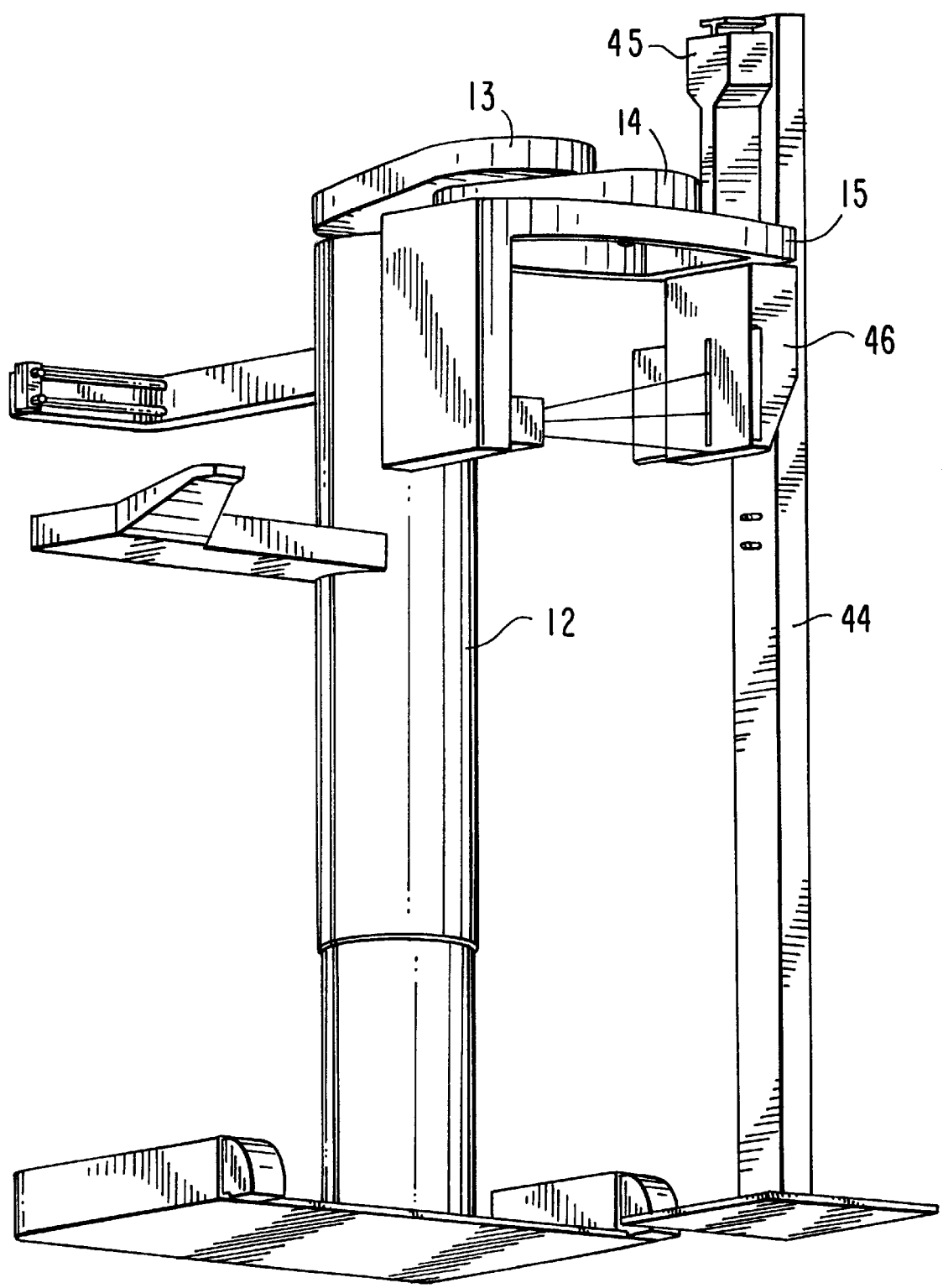
FIG. 16 shows a situation in which an x-ray recording device based on the use of a radiographic film is fetched from the storage post by means of the apparatus according to the invention.

In FIG. 16 the moving body parts 13, 14 and 15 of the apparatus according to the invention are shown rotated into a position having the x-ray detector mounting head of the fourth body part 15 brought close to the storage post 44. The first body part 12 of the apparatus is provided with a telescopic function for height adjustment. whereby the fourth body part 15 is brought level with the radiographic film holder 46. In this position the film holder 46 can be attached to the fourth body part 15.

Figure 17:
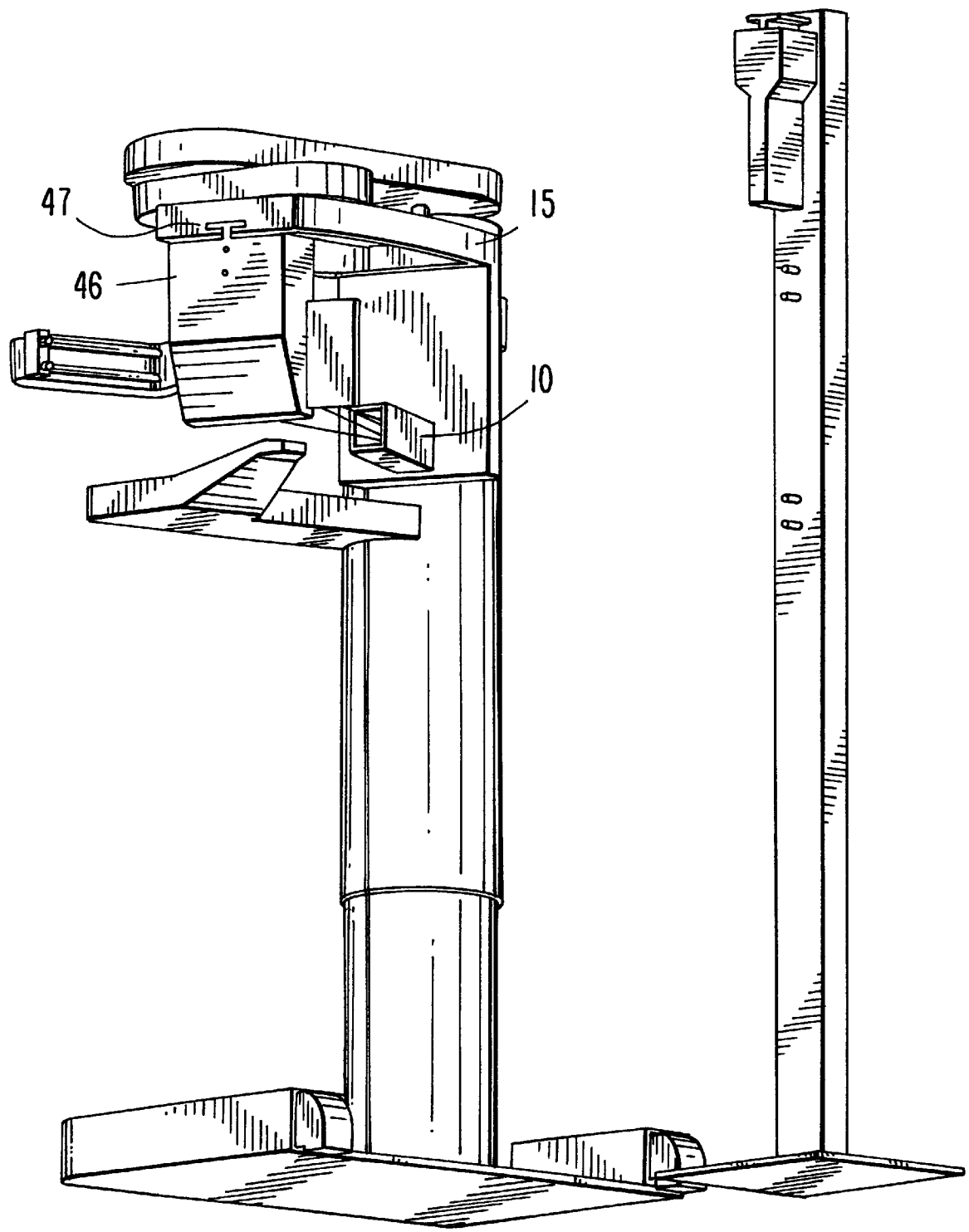
FIG. 17 shows a situation in which an x-ray recording device based on the use of a radiographic film is ready for use in the apparatus according to the invention.

In FIG. 17 the radiographic film holder 46 is shown attached to the fourth body part 15, opposite to the x-ray source 10 so that the apparatus according to the invention is set ready for a panoramic exposure. The film holder 46 is equipped with locking means compatible with the mounting groove 47. Obviously, any other type of mounting means can be used.

Figure 18:
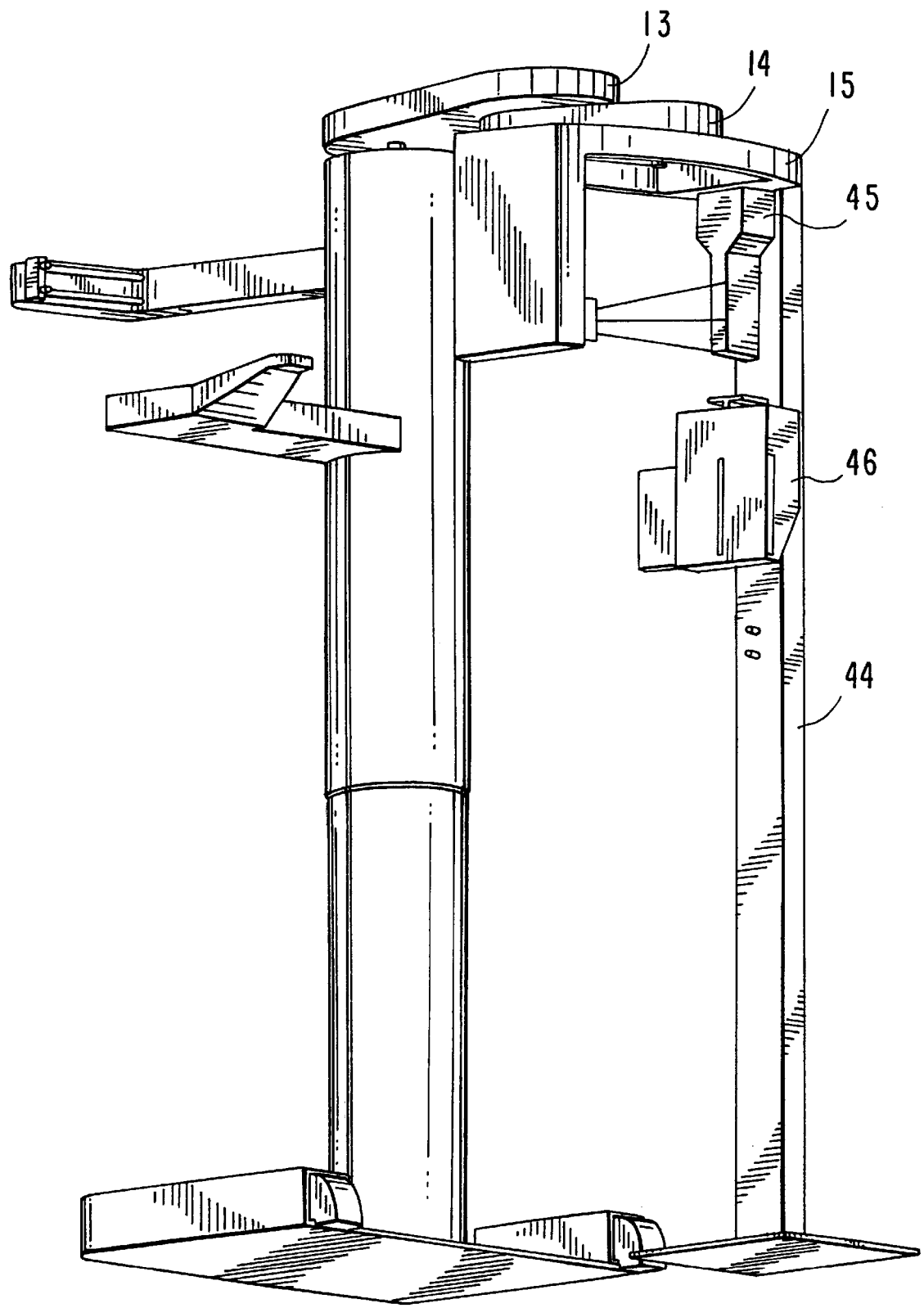
FIG. 18 shows a situation in which a digital x-ray recording device is fetched from the storage post by means of the apparatus according to the invention.

In FIG. 18 the moving body parts 13, 14 and 15 of the apparatus according to the invention are shown rotated into a position in which the detector mounting head of the fourth body part 15 is brought close to the storage post 44 and the fourth body part 15 is brought level with the digital x-ray detector 45. In this position the x-ray detector 45 can be attached to the fourth body part 15.

Figure 19:
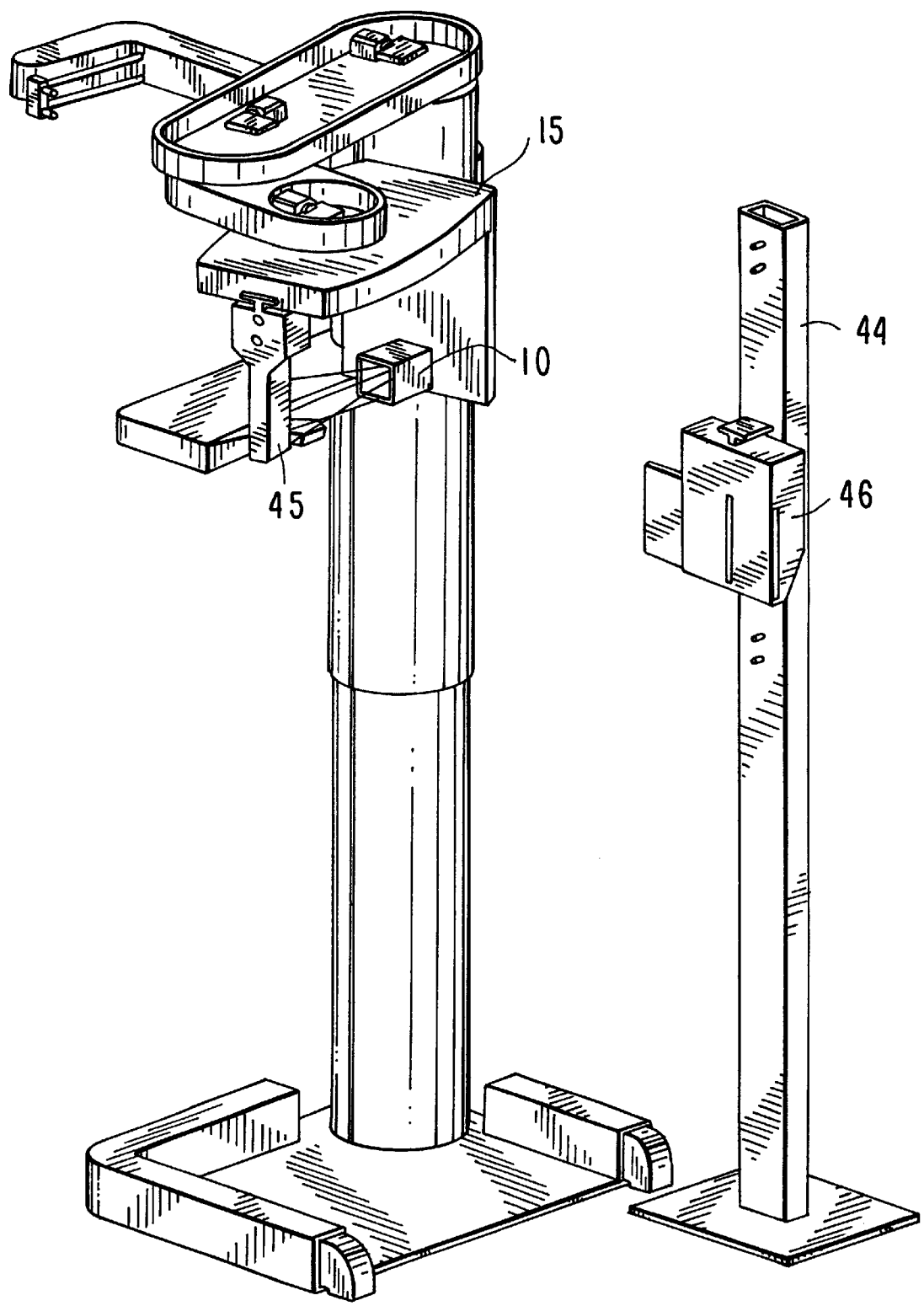
FIG. 19 shows a situation in which a digital x-ray recording device is ready for use in the apparatus according to the invention.

In FIG. 19 the digital x-ray detector 45 is shown attached to the fourth body part 15, opposite to the x-ray source 10 so that the apparatus according to the invention is set ready for a panoramic exposure. The digital x-ray detector 45 is equipped with locking means compatible with the mounting groove 47. Obviously, any other type of mounting means can be used.

Figure 20:
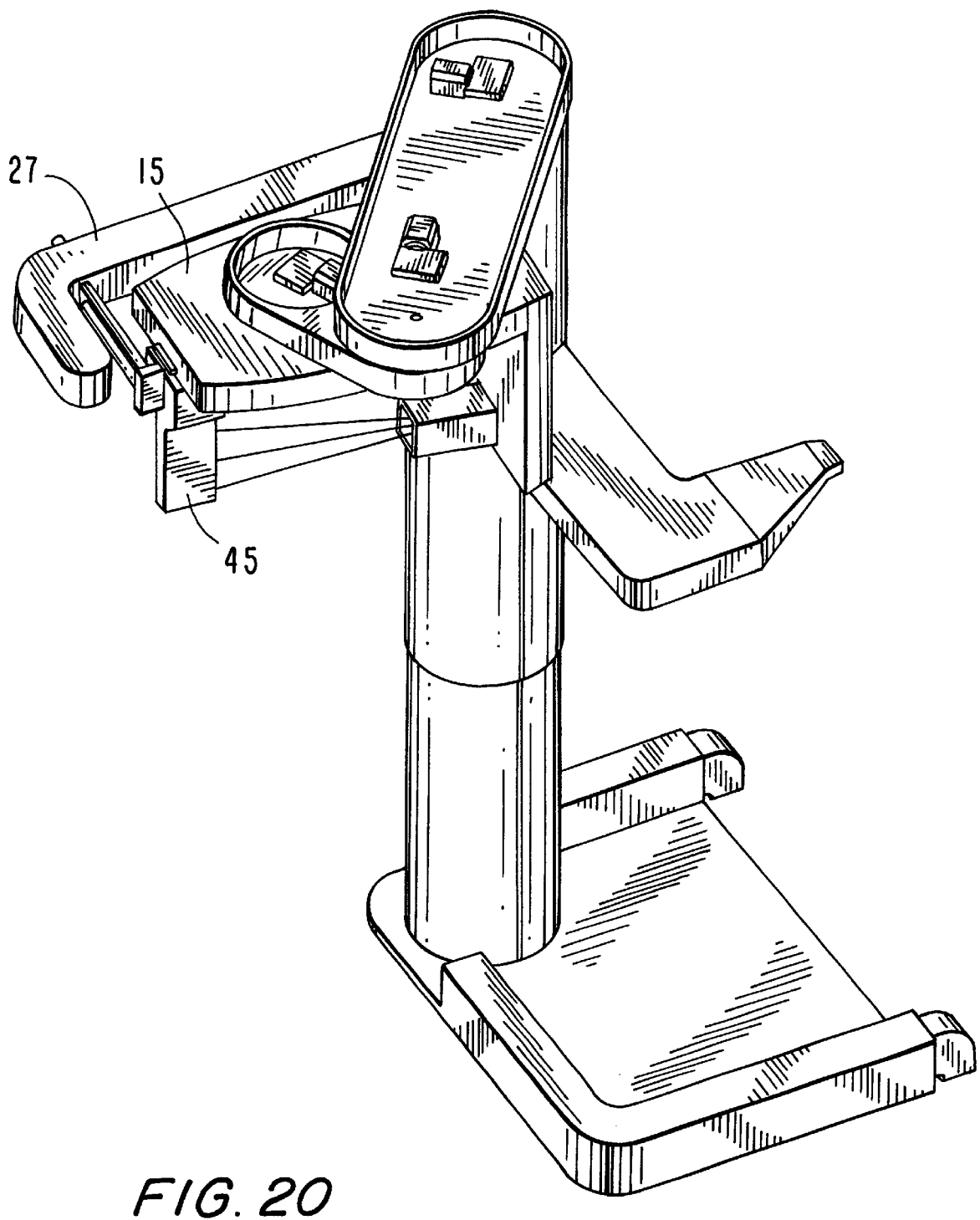
FIG. 20 shows a situation in which the x-ray recording device is moved to the cephalostat arm by means of the apparatus according to the invention.

In FIG. 20 is shown a situation in which the digital x-ray detector 45 is first fetched robotically from the storage post and then attached to the fourth body part 15. Next, the detector is taken robotically to the detector mounting head of the cephalostat support arm 27 and then attached to said cephalostat support arm 27. Obviously, any other type of radiographic recording means may be employed as the x-ray detector.

Figure 21:
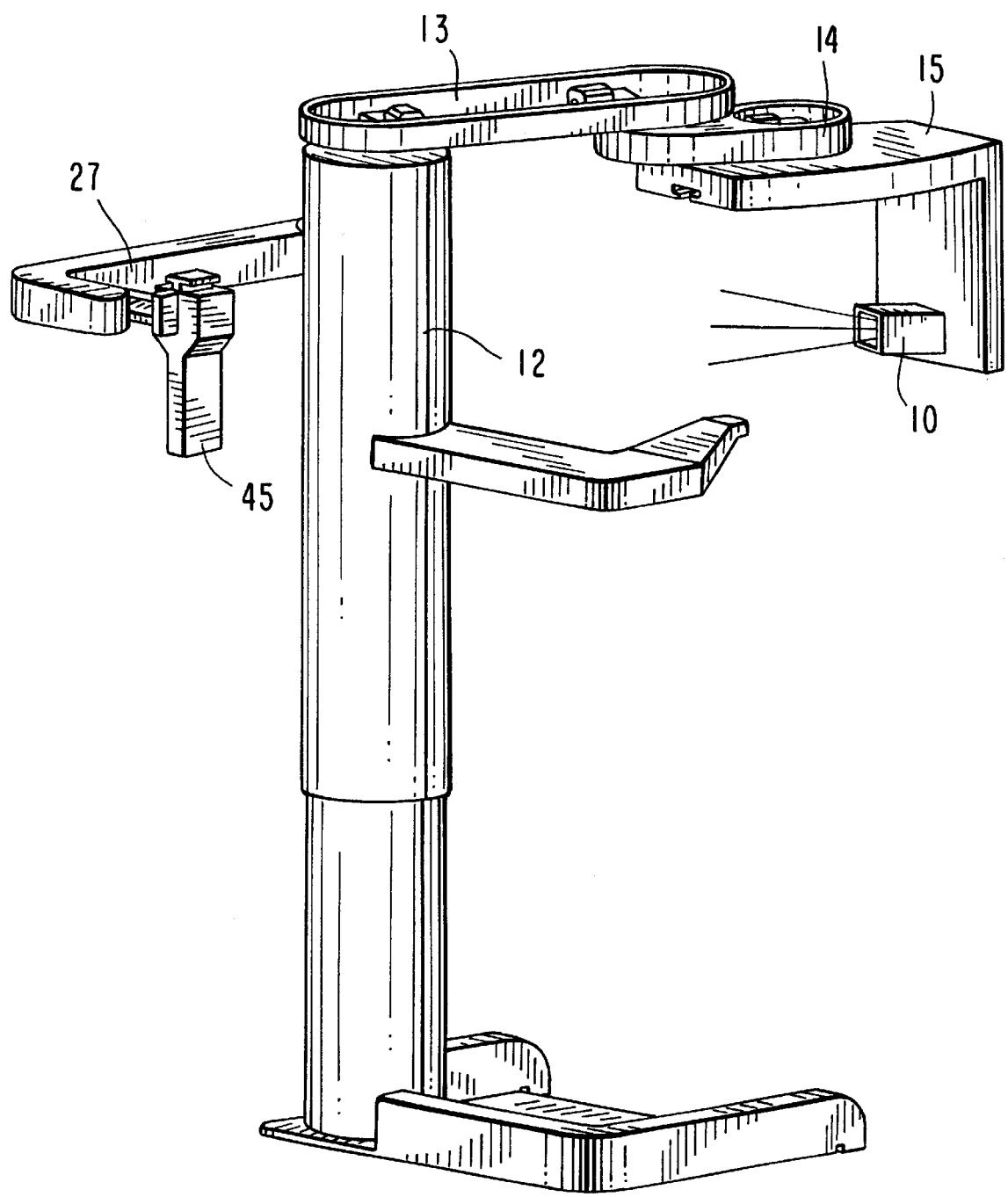
FIG. 21 shows the positions of the body parts in the apparatus according to the invention when set ready for a cephalographic exposure.
Figure 22:
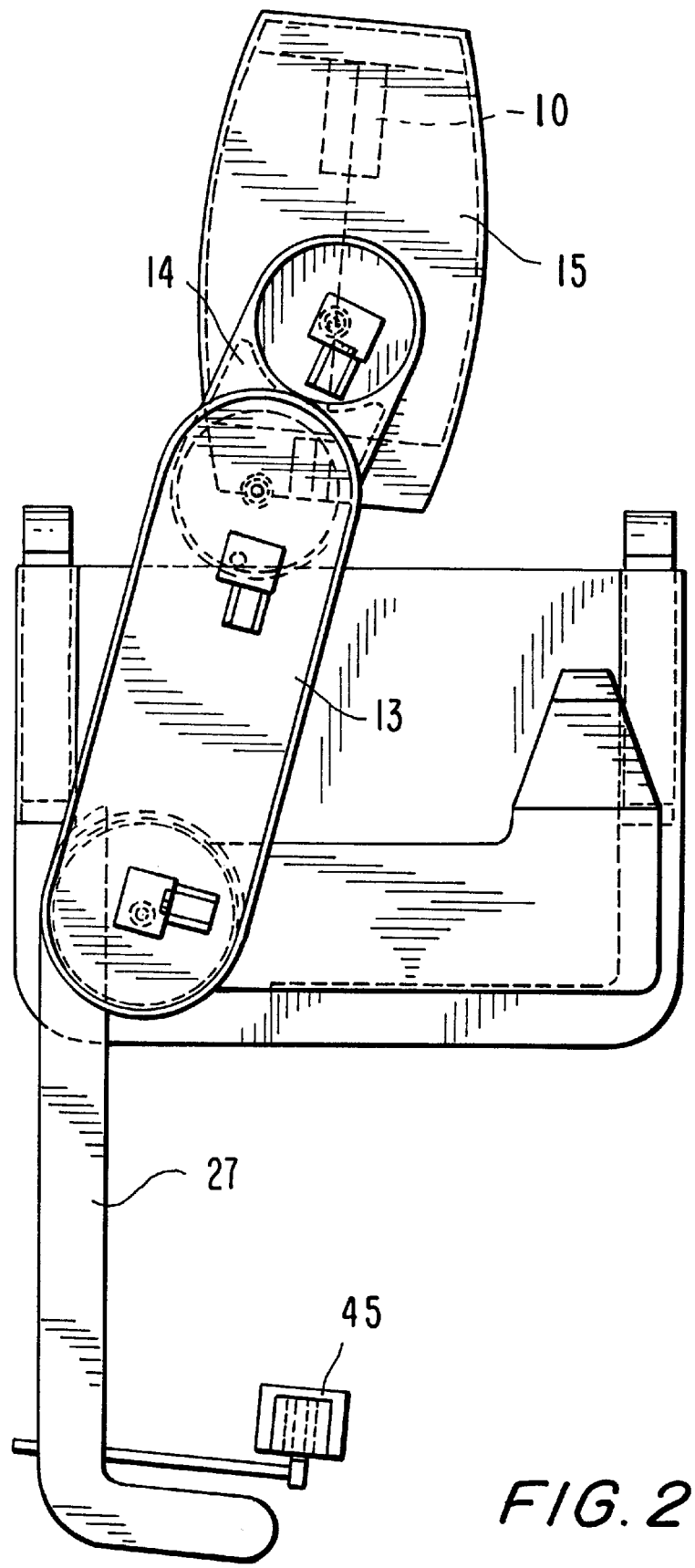
FIG. 22 shows the situation of FIG. 21 viewed from above.

In FIG. 21 the apparatus according to the invention is shown ready for a cephalometric exposure. The situation of FIG. 21 is otherwise similar to that of FIG. 11 with the exception of the detachable and freely transferable x-ray detector. FIG. 22 shows the situation of FIG. 21 viewed from above, thus giving a good overview of the mutual disposition and distances of the different components in the apparatus according to the invention.

In FIG. 23 is shown an alternative embodiment of the apparatus according to the invention having the fourth body part 15 replaced by two separate L-arms 54, 55. The x-ray source 10 is herein connected to the L-arm 54, while the other L-arm 55 carries the x-ray detector 20. The other body part is replaced by two arms 52, 53 operating in a superimposed disposition. This arrangement makes it possible to implement with the help of a simplified construction all the varied orbital geometries required in the different radiographic imaging modes. The embodiment illustrated in FIG. 23 is shown an alternative arrangement of configuring the SCARA arms of the apparatus according to the invention. This configuration disposes with a separate arm for, e.g., cephalometric exposures, inasmuch the arms can be taken sufficiently far apart from each other. Herein, the body parts 52 and 53 are connected to the first body part 12 by means of a common vertically-aligned pivot shaft, and the body part 52 carries the body part 54 connected thereto, while the body part 53 carries the body part 55 connected thereto. The x-ray source 10 is moved orbitally by means of the body parts 52 and 54, while the x-ray detector is moved orbitally by means of the body parts 53 and 55. Furthermore, the x-ray source 10 is adapted to rotate freely about the vertical axis in respect to the L-arm 54, and respectively, also the x-ray detector 20 in regard to the L-arm 55. The rotational movement of the x-ray source 10 and the x-ray detector 20 can be implemented with the help of active actuators, advantageously using stepping motors or the like pulse-controlled actuator devices. Using this type of construction, the apparatus according to the invention can implement all the above-mentioned radiographic imaging modes without needing separate accessories for, e.g., cephalography.

In FIG. 24 is shown the position of the arms during a cephalometric exposure. The body parts 52 and 54 are rotated almost to their extreme limit positions and, respectively, the body parts 53 and 55 are rotated in the opposite direction almost to their extreme limit positions. In this fashion, the x-ray source 10 and the x-ray detector 20 can be brought maximally apart from each other. The patient 17 is shown standing close to the x-ray detector 20.

Figure 25B:
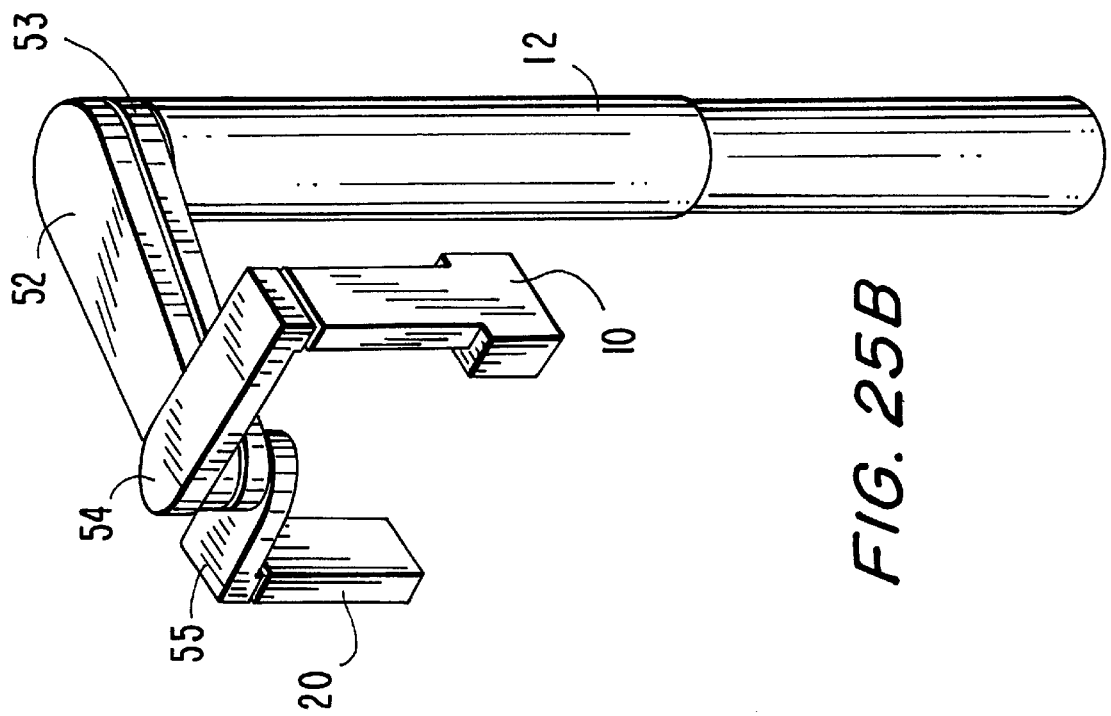
FIGS. 25A and 25B show the apparatus of FIG. 23 driven into positions corresponding to two different panoramic projections.
Figure 25A:
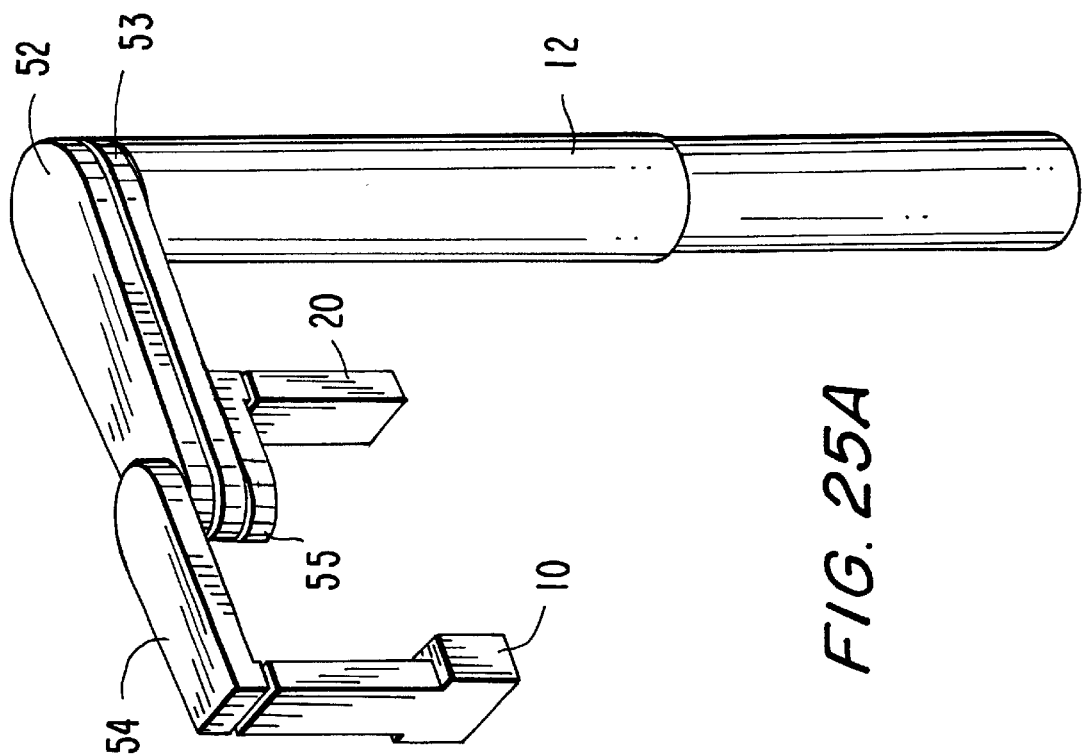

In FIGS. 25A and 25B the position of the SCARA arms is shown in an exemplifying manner for two different positions of a panoramic exposure. During both phases of the exposure, the body parts 52 and 53 can remain stationary in parallel to each other, while the body parts 54 and 55 generate the mutual orbital movement of the x-ray source 10 and the x-ray detector 20 as required for the panoramic imaging mode. In FIG. 25A, all the body parts of the arm systems are shown driven parallel to each other. In FIG. 25B, the body parts 54 and 55 are shown rotated into an almost orthogonal position in respect to the body parts 52 and 53. The other positions of the radiographic projections are formed by the intermediate positions between these extreme positions. A corresponding orbital geometry for a radiographic projection may alternatively be realized by way of not steering the body parts 52 and 53 into a superimposed position, but rather, controlling their position over a predetermined orbit. Simultaneously, the positions of the x-ray source 10 and the x-ray detector 20 must be rotated so as to keep them at all times facing each other in order to facilitate the recording of the transmitted x-ray beam.

Depending on the application, the above-described apparatus may be modified in varied ways within the scope of the inventive spirit of the present invention. In some embodiments of the invention, the other body part 13 may be attached to the first body part 12 in a fixed manner without using a pivot shaft. Alternatively, the second body part 13 can be mounted directly and solidly on a wall and/or ceiling, thus disposing with the first body part 12 of the apparatus, which hereby is replaced by said mounting on the wall and/or ceiling and the mounting blocks and fastening means used as fixtures. In this modification of the apparatus, it is possible to realize the radiographic imaging mode described above in conjunction with FIGS. 6A, 6B and 6C. However, the cephalostat construction shown in FIGS. 11 and 12 cannot be implemented in an apparatus according to this embodiment, not at least directly.

Finally, it must be noted that the apparatus according to the invention is shown in FIGS. 2–12 in its very schematic form and in practice there may be used a plurality of different accessories omitted from the drawings. When the x-ray detector 20 is a CCD sensor or the like, the apparatus naturally includes all the necessary electronics and display equipment capable of storing the radiographic image in a digital form and displaying the same on a screen, for instance. Furthermore, the apparatus can be complemented with any conventional storage/display system of patient data and other information.

To those versed in the art it obvious that the above-described preferred embodiment of the invention is nonlimiting to the scope and spirit of the invention that may be varied by their details in a plurality of ways.

The scope of the invention is defined in the appended claims.

What is claimed is:

1. A cranial radiography apparatus comprising:
a first body part;
a second body part having first and second ends, said second body part coupled to said first body part at said first end;
a third body part coupled to said second body part at said second end, said third body part being rotatable with respect to said second body part;
a first pivot shaft for coupling said third body part to said second body part at said second end;
a fourth body part coupled to said third body part said fourth body part being rotatable with respect to said third body part;
a second pivot shaft for coupling said fourth body part to said third body part;
an x-ray source coupled to a first end of said fourth body part;
an x-ray detector coupled to a second end of said fourth body part;
means for rotating said third body part;
means for rotating said fourth body part;
means for selectively controlling said means for rotating said third and fourth body parts to thereby enable said x-ray source and said x-ray detector to be moved along a selected orbit;
wherein said first and second pivot shafts are structured and arranged to be substantially parallel to one another and located at a constant fixed distance from one another.

2. The cranial radiography apparatus according to claim 1, wherein said fourth body part is a substantially c-shaped horizontal member;
wherein said first end of said fourth body part is structured and arranged to detachably secure said x-ray source; and
wherein said second end of said fourth body part is structured and arranged to detachably secure said x-ray detector.

3. The cranial radiography apparatus according to claim 1, wherein said fourth body part includes first and second substantially L-shaped arms adapted to be rotated around a vertical axis, said first L-shaped arm coupled to said x-ray source and said second L-shaped Arm coupled to said x-ray detector.

4. The cranial radiography apparatus according to claim 1, wherein said first body part is coupled to said second body part by means of a third pivot shaft; and said apparatus further comprising:
an active program-controlled actuator operably coupled to said third pivot shaft.

5. The cranial radiography apparatus according to claim 4, wherein an axis of said first pivot shaft is parallel to an axis of said second pivot shaft and wherein an axis of said third pivot shaft is parallel to said axis of said first and second pivot shafts.

6. The cranial radiography apparatus according to claim 1, wherein said first body part is permanently connected to said second body part.

7. The cranial radiography apparatus according to claim 1, wherein said second body part is mounted directly to one of a wall and ceiling.

8. The cranial radiography apparatus according to claim 1, further comprising a cephalostat mounted to said apparatus by means of a support arm coupled to one of said first and second body parts;
wherein said support arm is structured and arranged to be parallel to said second and third body parts and extends from an opposite side of said first body part relative to said second and third body parts.

9. The cranial radiography apparatus according to claim 1, wherein said first body part is a telescoping arm which permits a height adjustment of said second, third and fourth body parts.

10. The cranial radiography apparatus according to claim 1, wherein an axis of said first pivot shaft is parallel to an axis of said second pivot shaft.

11. The cranial radiography apparatus according to claim 10, wherein said axis of said first pivot shaft is vertically parallel to said axis of said second pivot shaft.

12. The cranial radiography apparatus according to claim 1, wherein said third and fourth body parts are structured and arranged to permit a manual positioning of said third and fourth body parts.

13. The cranial radiography apparatus according to claim 12, wherein said second is structured and arranged to permit a manual position of said second body part.

14. The cranial radiography apparatus according to claim 1, wherein said means for rotating said third body part is a first active actuator;
wherein said means for rotating said fourth body part is a second active actuator;
and wherein said means for selectively controlling said means for rotating said third and fourth body parts comprises a keyboard operably coupled to a central computing unit, a plurality of driver units operably coupled to said central computing unit and responsive to said central computing unit, said driver units being structured and arranged to control said first and second active actuators.

15. The cranial radiography apparatus according to claim 14, wherein said first and second active actuators are pulse-controlled stepping motors.

16. The cranial radiography apparatus according to claim 1, wherein said x-ray detector is one of a radiographic film with a cassette holder and transfer means thereof and a CCD sensor.

17. The cranial radiography apparatus according to claim 1, wherein said apparatus is structured and arranged to be collapsible into a compact configuration for one of transport and storage.

18. The cranial radiography apparatus according to claim 1, wherein said second body part is a single-member horizontal arm.

19. The cranial radiography apparatus according to claim 1, wherein said second body part comprises a first and second horizontal arms mounted one on top of the other.

20. The cranial radiography apparatus according to claim 1, further comprising:
a storage post for storing said x-ray detector.

21. The cranial radiography apparatus according to claim 20, wherein said x-ray detector is selectively detachable from said fourth body part to enable said detector to removed from said apparatus and stored in said storage post.

* * * * *